(12) United States Patent
Chen et al.

(10) Patent No.: US 7,521,464 B2
(45) Date of Patent: Apr. 21, 2009

(54) PYRAZOLE COMPOUNDS FOR TREATMENT OF NEURODEGENERATIVE DISORDERS

(75) Inventors: Yuhpyng L. Chen, Waterford, CT (US); Spiros Liras, Stonington, CT (US); Robert L. Rosati, Mystic, CT (US); Martin P. Allen, North Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/772,702

(22) Filed: Jul. 2, 2007

(65) Prior Publication Data

US 2007/0270474 A1 Nov. 22, 2007

Related U.S. Application Data

(63) Continuation of application No. 10/680,488, filed on Oct. 7, 2003, now Pat. No. 7,238,721.

(60) Provisional application No. 60/417,151, filed on Oct. 9, 2002.

(51) Int. Cl.
*A61K 31/41* (2006.01)
*C07D 231/02* (2006.01)

(52) U.S. Cl. .................................. 514/359; 548/371.7

(58) Field of Classification Search ........................ None
See application file for complete search history.

(56) References Cited

U.S. PATENT DOCUMENTS 7,238,721 B2  7/2007  Chen et al.

2002/0103185 A1  8/2002  Sanner et al.

FOREIGN PATENT DOCUMENTS

| EP | 0 885/890 | 2/1997 |
|---|---|---|
| WO | WO01/12188 | 2/2001 |
| WO | WO02/18346 | 3/2002 |
| WO | WO02/48114 | 6/2002 |
| WO | WO03/064396 | 8/2003 |

OTHER PUBLICATIONS

Rzepecki, et al., "Prevention Of Alzheimer's Disease-associated A Beta Aggregation By Rationally Designed Nonpeptidic Beta-Sheet Ligans," *The Journal Of Biological Chemistry*, 2004, 47497-47505, vol. 279, No. 46.

*Primary Examiner*—Kamal A Saeed
(74) *Attorney, Agent, or Firm*—Jeffrey H. Tidwell; Bryan C. Zielinski

(57) ABSTRACT

The invention provides compounds of Formula I:

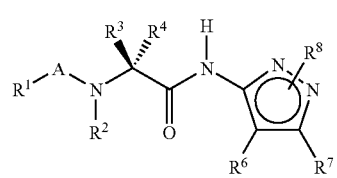

wherein $R^1$, $R^2$, $R^3$, $R^4$, $R^6$, $R^7$, $R^8$ and A are as defined. Compounds of formula I have activity inhibiting production of Aβ-peptide. The invention also provides pharmaceutical compositions and methods for treating diseases, for example Alzheimer's disease, in mammals comprising compounds of Formula I.

16 Claims, No Drawings

PYRAZOLE COMPOUNDS FOR TREATMENT OF NEURODEGENERATIVE DISORDERS

This application is a continuation of U.S. patent application Ser. No. 10/680,488, filed Oct. 7, 2003, now U.S. Pat. No. 7,238,721, which claims the benefit of U.S. Provisional Patent Application No. 60/417,151, filed Oct. 9, 2002, all of which are hereby incorporated by reference in their entirety.

FIELD OF THE INVENTION

The present invention relates to treatment of Alzheimer's disease and other neurodegenerative disorders in mammals, including in humans. This invention also relates to inhibiting in mammals, including in humans, the production of β-amyloid peptides (Aβ-peptides) which can contribute to formation of neurological deposits of amyloid protein. More particularly, this invention relates to pyrazole compounds useful for treatment of neurological disorders, such as Alzheimer's disease and Down's Syndrome, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CAA) and prion-mediated diseases (see, e.g., Haan et al. *Clin. Neurol. Neurosurg.* 1990, 92 (4):305-310; Glenner et al. *J Neurol. Sci.* 1989, 94:1-28). AD affects nearly half of all people past the age of 85, the most rapidly growing portion of the United States population. As such, the number of AD patients in the United States is expected to increase from about 4 million to about 14 million by the middle of the next century.

Treatment of AD typically is the support provided by a family member in attendance. Stimulated memory exercises on a regular basis have been shown to slow, but not stop, memory loss. A few drugs, for example Aricep™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, are the basis for definitive pathological diagnosis of AD.

The major components of amyloid plaques are the amyloid Aβ-peptides, also called Aβ-peptides, which consist of three proteins having 40, 42 or 43 amino acids, designated as the $A\beta_{1-40}$, $A\beta_{1-42}$, and $A\beta_{1-43}$ peptides, respectively. The Aβ-peptides are thought to cause nerve cell destruction, in part, because they are toxic to neurons in vitro and in vivo.

The Aβ peptides are derived from larger β-amyloid precursor proteins (APP proteins), which consist of four proteins containing 695, 714, 751 or 771 amino acids, designated as the $APP_{695}$, $APP_{714}$, $APP_{751}$ and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. APP is cleaved by alpha- and beta-secretases, causing the release of soluble derivatives of protein ((α-APPs and β-APPs) and the retention of membrane-bound 83- and 99-amino acid fragments (C83 and C99). These fragments are substrates for the enzyme gamma-secretase. Gamma-secretase produces the Aβ-peptide fragment from C99 and p3 from C83. Gamma-secretase and beta-secretase inhibitors are thus expected to inhibit the production of Aβ-peptide. (Haass, C. and Selkoe, D. J. 1993 *Cell* 75:1039-1042; Selkoe, D. J. et. al. *Annu. Rev. Cell Biol.* 10, 373-403 (1994); Wolfe, M. S. et. al., *Nature*, 398, 513).

This invention relates to novel compounds that inhibit Aβ-peptide production, to pharmaceutical compositions comprising such compounds, and to methods of using such compounds to treat neuorodegenerative disorders.

SUMMARY OF THE INVENTION

The present invention provides compounds of Formula:

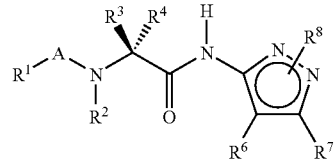

wherein:

A is selected from —C(=O)C(=O)—, —C(=O)Z—, —C(=S)Z—, —C(=NR$^5$)Z—, and —S(O)$_2$—;

wherein Z is —CH$_2$—, —CH(OH)—, —CH(OC(=O)R$^{11}$)—, —CH(NH$_2$)—, —CH(CH$_2$(OH))—, —CH(CH(C$_1$-C$_4$ alkyl)(OH))—, or —CH(C(C$_1$-C$_4$ alkyl)(C$_1$-C$_4$ alkyl)(OH))—, for example —CH(C(CH$_3$)(CH$_3$)(OH))— or —CH(C(CH$_3$)(CH$_2$CH$_3$)(OH))—;

R$^1$ is selected from C$_1$-C$_{20}$ alkyl and —C$_1$-C$_{20}$ alkoxy, C$_3$-C$_8$ cycloalkyl, (C$_4$-C$_8$)cycloalkenyl, (C$_5$-C$_{11}$)bi- or tricycloalkyl, (C$_7$-C$_{11}$)bi- or tricycloalkenyl, (3-8 membered) heterocycloalkyl, (C$_6$-C$_{14}$)aryl, or (5-14 membered) heteroaryl, wherein said alkyl and alkoxy each optionally contains from one to five double or triple bonds, and wherein each hydrogen atom of said alkyl and alkoxy is optionally replaced with a fluorine;

wherein when R$^1$ is alkyl or alkoxy, R$^1$ is optionally substituted with from one to three substituents R$^{1a}$, and wherein when R$^1$ is cycloalkyl, cycloalkenyl, bi- or tricycloalkyl, bi- or tricycloalkenyl, heterocycloalkyl, aryl, or heteroaryl, then R$^1$ is optionally substituted with from one to three substituents R$^{1b}$;

R$^{1a}$ is in each instance independently selected from —OH, —C$_1$-C$_6$ alkyl independently optionally containing from one to three double or triple bonds, —C$_1$-C$_6$ alkoxy independently optionally containing from one to three double or triple bonds, —Cl, —F, —Br, —I, —CN, —NO$_2$, —NR$^9$R$^{10}$, —C(=O)NR$^9$R$^{10}$, —S(O)$_n$NR$^9$R$^{10}$, —C(=O)R$^{11}$, —S(O)$_n$R$^{11}$, —C(=O)OR$^{12}$, —C$_3$-C$_8$ cycloalkenyl, —C$_4$-C$_8$ cycloalkenyl, —(C$_5$-C$_{11}$)bi- or tricycloalkyl, —(C$_7$-C$_{11}$) bi- or tricycloalkenyl, -(3-8 membered) heterocycloalkyl, —(C$_6$-C$_{14}$)aryl, -(5-14 membered) heteroaryl, —(C$_6$-C$_{14}$) aryloxy, and -(5-14 membered) heteroaryloxy, wherein said alkyl, alkoxy, cycloalkyl, cycloalkenyl, bi- or tricycloalkyl, bi- or tricycloalkenyl, heterocycloalkyl, aryl, heteroaryl, aryloxy, and heteroaryloxy are each independently optionally substituted with from one to three R$^{1b}$ substituents;

R$^{1b}$ is in each instance independently selected from —Cl, —F, —Br, —I, —CN, —NO$_2$, —(C$_{zero}$-C$_4$ alkylene)— NR$^9$R$^{10}$, —(C$_{zero}$-C$_4$ alkylene)—C(=O)NR$^9$R$^{10}$, —(C$_{zero}$-C$_4$ alkylene)—C(=O)R$^{11}$, —(C$_{zero}$-C$_4$ alkylene)—C(=O)

$OR^{12}$, —($C_{zero}$-$C_4$ alkylene)—$S(O)_nR^{11}$, —($C_{zero}$-$C_4$ alkylene)—$S(O)_nNR^9R^{10}$, —($C_{zero}$-$C_4$ alkylene)—OH, —$C_1$-$C_6$ alkyl independently optionally containing from one to three double or triple bonds, —$C_1$-$C_6$ alkoxy independently optionally containing from one to three double or triple bonds, —$C_1$-$C_6$ hydroxyalkyl, —($C_6$-$C_{14}$) aryloxy, -(5-14 membered) heteroaryloxy, —($C_6$-$C_{14}$) aryl, -(5-15 membered) heteroaryl, and —$C_1$-$C_6$ alkyl independently optionally containing from one to three double or triple bonds and independently substituted with from one to six atoms independently selected from F, Cl, Br, and I;

$R^2$ is selected from —H, —$C_1$-$C_4$ alkyl optionally containing one or two double or triple bonds, —C(=O)($C_1$-$C_4$ alkyl), —$C_6$-$C_{10}$ aryl, —$SO_2$—($C_6$-$C_{10}$ aryl), and —$SO_2$—$CH_2$—($C_6$-$C_{10}$ aryl), and $R^2$ is optionally substituted with from one to three substituents $R^{1b}$;

$R^3$ is selected from $C_1$-$C_6$ alkyl, —$C_2$-$C_6$ alkenyl, —$C_2$-$C_6$ alkynyl, —($C_{zero}$-$C_4$ alkylene)-($C_3$-$C_6$ cycloalkyl), and —($C_{zero}$-$C_4$ alkylene)-($C_3$-$C_6$ cycloalkenyl), wherein said alkyl, alkenyl and alkynyl are each optionally substituted with a substituent selected from —OH, $C_1$-$C_4$ alkoxy, and —S—($C_1$-$C_4$ alkyl);

$R^4$ is H, D, F, or $C_1$-$C_4$ alkyl;

or $R^3$ and $R^4$ may together optionally form a cyclopropyl, cyclobutyl, cyclopentyl, cyclohexyl, morpholino, piperidino, or perhydro-2H-pyran moiety, wherein said moiety formed by $R^3$ and $R^4$ is optionally substituted with one to three substituents independently selected from —OH, —Cl, —F, —CN, —$CF_3$, methyl, ethyl, methoxy, ethoxy, allyl, and —$OCF_3$;

$R^5$ is selected from —H, —$C_1$-$C_6$ alkyl optionally substituted with from one to three $R^{1a}$ groups, and —$C_6$-$C_{10}$ aryl optionally substituted with from one to three $R^{1a}$;

or $R^5$ and $R^1$ may together optionally form a five to fourteen membered heteroaryl ring or a five to eight membered heterocycloalkyl ring, wherein said heteroaryl or heterocycloalkyl ring optionally contains one or two further heteroatoms selected from N, O, and S, and wherein said heterocycloalkyl ring optionally contains from one to three double bonds, and wherein said heteroaryl or heterocycloalkyl ring is optionally substituted from one to three substituents $R^{1b}$ groups;

$R^6$ is selected from —H, —$C_1$-$C_{20}$ alkyl, —Cl, —F, —Br, —I, —CN, —$CF_3$, —C(=O)$R^{11}$, —C(=O)$OR^{12}$, —$S(O)_n$NR$^9$R$^{10}$, —$S(O)_nR^{11}$, —C(=$NR^9$)$R^{15}$, —($C_3$-$C_{12}$) cycloalkyl, —($C_4$-$C_{12}$) cycloalkenyl, and —$C_6$-$C_{10}$ aryl, wherein said alkyl, alkylene, cycloalkyl, cycloalkenyl, and aryl of $R^6$ are each optionally substituted with from one to three $R^{1b}$ substituents;

$R^7$ is selected from H, —Cl, —F, —Br, —I, —CN, —$NO_2$, —NR$^{14}$R$^{15}$, —$CF_3$, —C(=O)NR$^{14}$R$^{15}$, —C(=O)R$^{13}$ $S(O)_n$ R$^{13}$—C(=O)OR$^{13}$, —C(=NR$^9$)R$^{15}$, —$S(O)_n$NR$^{14}$R$^{15}$, —$C_1$-$C_{20}$ alkyl, —$C_1$-$C_{20}$ alkoxy, —($C_{zero}$-$C_4$ alkylene)-($C_3$-$C_{12}$ cycloalkyl), —($C_{zero}$-$C_4$ alkylene)-(($C_4$-$C_{12}$)cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricibalkenyl), —($C_{zero}$-$C_4$ alkylene)-((3-12 membered) heterocycloalkyl), —($C_{zero}$-$C_4$ alkylene)-((7-20 membered) heterobi- or heterotricycloalkyl), —($C_{zero}$-$C_4$ alkylene)-(($C_6$-$C_{14}$)aryl), and —($C_{zero}$-$C_4$ alkylene)-((5-15 membered) heteroaryl); wherein $R^7$ is optionally substituted with from one to three substituents independently selected from $R^{1a}$, —($CH_2$)$_{1-10}$NR$^9$R$^{10}$, —$C_3$-$C_{12}$ cycloalkyl, —((4-12 membered) heterocycloalkyl), —($C_6$-$C_{14}$) aryl, —((5-15 membered) heteroaryl), —(4-12 membered) heterocycloalkoxy), —($C_6$-$C_{12}$) aryloxy and -((5-12 membered) heteroaryloxy); said cycloalkyl, cycloalkenyl, bi- or tricycloalkyl, bi- or tri- cycloalkenyl, heterocycloalkyl, aryl, and heteroaryl of $R^7$ are each optionally and independently substituted with from one to six F; said alkyl, alkoxy, and alkylene of $R^7$ each optionally contains from one to five double or triple bonds; and each hydrogen atom of said alkyl, alkoxy, and alkylene of $R^7$ is independently optionally replaced with a fluorine;

or $R^5$ and $R^7$ or $R^7$ and its proximate nitrogen atom may together optionally form a —($C_6$-$C_{10}$) aryl ring, —($C_6$-$C_8$) cycloalkyl or cycloalkenyl ring, a five to eight membered heterocycloalkyl or heterocycloalkenyl ring, a —($C_{10}$-$C_{14}$) membered bicycloalkyl or bicycloalkenyl ring, or a ten to fourteen membered bicycloheteroalkyl or bicycloheteroalkenyl ring fused to the pyrazole ring of Formula I, wherein from one to three members of said heterocycloalkyl and heterocycloalkenyl rings, and from one to five members of said bicycloheteroalkyl and bicycloheteroalkenyl rings are selected independently from N, O and S, and wherein said aryl, cycloalkyl, cycloalkenyl, heterocycloalkyl, heterocycloalkenyl, bicycloalkyl, bicycloalkenyl, bicycloheteroalkyl, and bicycloheteroalkenyl rings optionally are substituted with from one to three $R^{1b}$ groups;

$R^8$ is selected from —H, —$C_1$-$C_4$ alkyl, —Cl, —F, —Br, —I, —CN, —$CF_3$, —C(=O)$R^{11}$, —C(=O)$OR^{12}$, and —$C_6$-$C_{10}$aryl, with the proviso that the pyrazole ring is always aromatic and that $R^8$ is attached to either ring nitrogen;

$R^9$ and $R^{10}$ are each independently selected from —H, —OH, —$C_1$-$C_6$ alkyl independently optionally containing from one to three double or triple bonds and wherein each hydrogen is independently optionally replaced with a fluorine, —$C_1$-$C_6$ alkoxy independently optionally containing from one to three double or triple bonds and wherein each hydrogen is independently optionally replaced with a fluorine, —C(=O)$R^{11}$, —$S(O)_nR^{11}$, —C(=O)$OR^{12}$, —$S(O)_n$NR$^{11}$R$^{12}$, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-($C_6$-$C_{14}$ aryl), —($C_{zero}$-$C_4$ alkylene)-(3-8 membered heterocycloalkyl), and —($C_{zero}$-$C_4$ alkylene)-(5-14 membered heteroaryl), wherein said cycloalkyl, cycloalkenyl, bi-or tricycloalkyl, bi- or tricycloalkenyl, aryl, heterocycloalkyl, and heteroaryl are each optionally independently substituted with from one to three substituents independently selected from —Cl, —F, —Br, —I, —CN, —$NO_2$, —NR$^{14}$R$^{15}$, —C(=)ONR$^{14}$R$^{15}$, —C(=O)$R^{11}$, —C(=O)$OR^{12}$, —$S(O)_n$ $R^{11}$, —$S(O)_n$NR$^{14}$R$^{15}$, —OH, —$C_1$-$C_6$ alkyl independently optionally containing from one to three double or triple bonds, —$C_1$-$C_6$ alkoxy independently optionally containing from one to three double or triple bonds, —$C_1$-$C_6$ hydroxyalkyl, —($C_6$-$C_{14}$) aryloxy, -(5-14 membered) heteroaryloxy, —($C_{zero}$-$C_4$)-(($C_6$-$C_{14}$) aryl), —($C_{zero}$-$C_4$)-(5-14 membered heteroaryl), and -$C_1$-$C_6$ alkyl independently optionally containing from one to three double or triple bonds and independently substituted with from one to six atoms independently selected from F, Cl, Br, and I;

or NR$^9$R$^{10}$ can independently optionally form a heterocycloalkyl moiety of from four to seven ring members, said heterocycloalkyl moiety independently optionally comprising one or two further heteroatoms independently selected from N, O, and S, and independently optionally containing from one to three double bonds, and said heterocycloalkyl moiety independently optionally substituted with from one to three substituents independently selected from —Cl, —F, —Br, —I, —CN, —$NO_2$, —NR$^{14}$R$^{15}$, —C(=)ONR$^{14}$R$^{15}$, —C(=O)$R^{11}$, —C(=O)$OR^{12}$, —$S(O)_nR^{11}$, —$S(O)_n$NR$^{14}$R$^{15}$, —OH, —$C_1$-$C_6$ alkyl independently optionally containing from one to three double or triple bonds, —$C_1$-$C_6$ alkoxy independently optionally containing from one to three double or triple bonds, —$C_1$-$C_6$ hydroxyalkyl independently optionally containing from one to three double or triple bonds, —($C_6$-$C_{14}$) aryloxy, -(5-14 membered) heteroaryloxy, —($C_{zero}$-$C_4$)-(($C_6$-$C_{14}$) aryl), —($C_{zero}$-$C_4$)-(5-14 membered heteroaryl), and —$C_1$-$C_6$ alkyl independently optionally containing from one to three double or triple bonds and independently substituted with from one to six atoms independently selected from F, Cl, Br, and I;

$R^{11}$ and $R^{12}$ are each independently selected from H, —$C_1$-$C_6$ alkyl, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), and —($C_{zero}$-$C_4$ alkylene)-(($C_7$-$C_{11}$)bi- or tricycloalkenyl), —($C_{zero}$-$C_4$ alkylene)-($C_6$-$C_{10}$ aryl), —($C_{zero}$-$C_4$ alkylene)-((3-8 membered) heterocycloalkyl), and —($C_{zero}$-$C_4$ alkylene)-((5-14 membered) heteroaryl), and $R^{11}$ and $R^{12}$ are independently optionally substituted with from one to three $R^{1b}$;

$R^{13}$ is selected from H, —$C_1$-$C_6$ alkyl optionally containing from one to three double or triple bonds and wherein each hydrogen is independently optionally replaced with a fluorine, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), and —($C_{zero}$-$C_4$ alkylene)-(($C_7$-$C_{20}$)bi- or tricycloalkenyl), —($C_{zero}$-$C_4$ alkylene)-($C_6$-$C_{14}$ aryl), —($C_{zero}$-$C_4$ alkylene)-((3-12 membered) heterocycloalkyl), —($C_{zero}$-$C_4$ alkylene)-((7-20 membered) heterobi- or heterotricycloalkyl), and —($C_{zero}$-$C_4$ alkylene)-((5-14 membered) heteroaryl), and $R^{13}$ is optionally substituted with from one to three substituents $R^{1b}$;

$R^{14}$ and $R^{15}$ are each independently selected from —H, —$C_1$-$C_{20}$ alkyl independently optionally containing from one to five double or triple bonds and wherein each hydrogen is independently optionally replaced with a fluorine, —C(=O)$R^{11}$, —S(O)$_n$$R^{11}$, —C(=O)O$R^{12}$, —S(O)$_n$N$R^{11}$$R^{12}$, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricycloalkenyl), —($C_{zero}$-$C_4$ alkylene)-($C_6$-$C_{14}$ aryl), —($C_{zero}$-$C_4$ alkylene)-(3-8 membered heterocycloalkyl), and —($C_{zero}$-$C_4$ alkylene)-(5-14 membered heteroaryl), wherein said cycloalkyl, cycloalkenyl, bi-or tricycloalkyl, bi- or tricycloalkenyl, aryl, heterocycloalkyl, and heteroaryl are each independently optionally substituted with from one to three substituents independently selected from —$C_1$-$C_6$ alkyl independently optionally containing from one to three double or triple bonds and wherein each hydrogen is independently optionally replaced with fluorine, —Cl, —F, —Br, —I, —CN, —$NO_2$, —$NH_2$, —OH, —C(=O)H, —S(O)$_n$H, —C(=O)OH, —C(=O)$NH_2$, —S(O)$_n$$NH_2$, —$C_1$-$C_6$ alkoxy independently optionally containing from one to three double or triple bonds and wherein each hydrogen is independently optionally replaced with fluorine, —$C_1$-$C_6$ hydroxyalkyl independently optionally containing from one to three double or triple bonds and wherein each hydrogen is independently optionally replaced with fluorine, -(5-14 membered) heteroaryloxy, —($C_6$-$C_{14}$ aryloxy), —($C_{zero}$-$C_4$ alkylene)-($C_6$-$C_{14}$ aryl), —($C_{zero}$-$C_4$ alkylene)-((5-14 membered) heteroaryl), and —$C_1$-$C_6$ alkyl independently substituted with from one to six atoms independently selected from F, Cl, Br, and I and independently optionally containing from one to three double or triple bonds;

or $NR^{14}R^{15}$ can independently optionally form a heterocycloalkyl moiety of from four to seven ring members, said heterocycloalkyl moiety independently optionally comprising one or two further heteroatoms independently selected from N, O, and S, and independently optionally containing from one to three double bonds, and said heterocycloalkyl moiety independently optionally substituted with from one to three substituents independently selected from —$C_1$-$C_6$ alkyl independently optionally containing from one to three double or triple bonds and wherein each hydrogen is independently optionally replaced with fluorine, —Cl, —F, —Br, —I, —CN, —$NO_2$, —$NH_2$, —OH, —C(=O)H, —S(O)$_n$H, —C(=O)OH, —C(=O)$NH_2$, —S(O)$_n$$NH_2$, —$C_1$-$C_6$ alkoxy independently optionally containing from one to three double or triple bonds and wherein each hydrogen is independently optionally replaced with fluorine, —$C_1$-$C_6$ hydroxyalkyl independently optionally containing from one to three double or triple bonds and wherein each hydrogen is independently optionally replaced with a fluorine, -(5-14 membered) heteroaryloxy, —($C_6$-$C_{14}$ aryloxy), —($C_{zero}$-$C_4$ alkylene)-($C_6$-$C_{14}$ aryl), —($C_{zero}$-$C_4$ alkylene)-((5-14 membered) heteroaryl), and —$C_1$-$C_6$ alkyl independently optionally containing from one to three double or triple bonds and independently substituted with from one to six atoms independently selected from F, Cl, Br, and I; and n is in each instance an integer independently selected from zero, 1, 2, and 3;

and pharmaceutically-acceptable salts thereof.

Compounds of Formula I inhibit production of Aβ-peptide. Compounds of Formula I and their pharmaceutically acceptable salts are therefore useful in treating neurodegenerative disorders, for example AD, in mammals, including humans.

In one embodiment, the present invention provides compounds of Formula I wherein A is —C(=O)Z— or —C(=O)C(=O)—. If A is —C(=O)Z—, then Z is preferably —$CH_2$— or —CH(OH)—.

In another embodiment, the invention provides compounds of Formula I wherein $R^3$ is $C_1$-$C_4$ alkyl wherein each hydrogen is independently optionally replaced with a fluorine. In another embodiment $R^3$ is allyl. In another embodiment $R^3$ is methyl, ethyl, n-propyl, n-butyl, i-butyl, s-butyl, or —$CH_2CH_2SCH_3$.

In another embodiment, the present invention provides compounds of Formula I wherein $R^6$ is selected from hydrogen, methyl, ethyl, —F, —Cl, —Br, and —$CF_3$.

In another embodiment the present invention provides compounds of Formula I wherein $R^1$ is —$C_2$-$C_{12}$ alkyl, $C_3$-$C_8$ cycloalkyl, ($C_5$-$C_8$)cycloalkenyl, —($C_5$-$C_{11}$)bi- or tricycloalkyl, —($C_7$-$C_{11}$)bi- or tricycloalkenyl, (3-8 membered) heterocycloalkyl), —($C_6$-$C_{10}$)aryl, -(5-10 membered) heteroaryl, or $C_1$-$C_4$ alkyl substituted with $R^{1a}$ wherein $R^{1a}$ is —($C_6$-$C_{10}$)aryl or -(5-10 membered) heteroaryl.

In another embodiment, the present invention provides compounds of Formula I wherein $R^1$ is $C_2$-$C_{10}$ alkyl, $C_3$-$C_{10}$ cycloalkyl, or —($C_7$-$C_{11}$)bicycloalkyl, wherein said alkyl optionally contains from one to five double bonds, and wherein each hydrogen atom of said alkyl may optionally be replaced with a fluorine.

When $R^1$ is $C_2$-$C_{10}$ alkyl, in one embodiment, $R^1$ is straight-chain. In another embodiment when $R^1$ is $C_2$-$C_{10}$ alkyl, $R^1$ is branched $C_3$-$C_{10}$ alkyl.

In another embodiment, $R^1$ is $C_3$-$C_{10}$ alkyl comprising a tertiary carbon, for example i-propyl or 2-methylpropyl. In another embodiment, $R^1$ is $C_4$-$C_{10}$ alkyl comprising a quaternary carbon, for example t-butyl.

In a further embodiment, $R^1$ is selected from phenyl, thienyl, and pyridyl, optionally and independently substituted with one or two substituents $R^{1b}$. When $R^1$ is phenyl, thienyl, or pyridyl substituted optionally with one or two substituents $R^{1b}$, then each $R^{1b}$ is preferably independently selected from —$C_1$-$C_4$ alkyl (in different embodiments, independently optionally containing one or two double or triple bonds), $CF_3$, —$C_1$-$C_4$ alkoxy (in different embodiments, independently optionally containing one or two double or triple bonds), —F, —Cl, —Br, phenyl, and phenoxy.

In a further embodiment, $R^1$ is phenyl or pyridyl and is optionally substituted with one or two substituents $R^{1b}$ independently selected from —F, —Cl and —$CF_3$.

In another embodiment $R^1$ is $C_3$-$C_7$ cycloalkyl, for example [2.2.1]-heptanyl.

In each of the aforementioned embodiments, A is preferably —C(=O)Z— or —C(=O)C(=O)—, Z preferably being —$CH_2$— or —CH(OH)—. Furthermore, $R^3$ is preferably $C_1$-$C_4$ alkyl, for example methyl, ethyl, n-propyl, n-butyl, i-butyl, s-butyl, or $R^3$ is allyl or —$CH_2CH_2SCH_3$, and $R^6$ is preferably hydrogen, methyl, ethyl, —F, —Cl, —Br, and —$CF_3$.

In a further embodiment, A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl,. —F, —Cl, —Br, and —$CF_3$; and $R^1$ is —$C_2$-$C_{12}$ alkyl, $C_3$-$C_8$ cycloalkyl, ($C_5$-$C_8$) cycloalkenyl, —($C_5$-$C_{11}$)bi- or tricycloalkyl, —($C_7$-$C_{11}$)bi- or tricycloalkenyl, -((3-8 membered) heterocycloalkyl), —($C_6$-$C_{10}$)aryl, —(5-10 membered) heteroaryl, or $C_1$-$C_4$ alkyl substituted with $R^{1a}$ wherein $R^{1a}$ is —($C_6$-$C_{10}$)aryl or -(5-10 membered) heteroaryl.

In another embodiment, the present invention provides compounds of Formula I wherein A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl, —F, —Cl, —Br, and —$CF_3$; and $R^1$ is $C_2$-$C_{10}$ alkyl, $C_3$-$C_{10}$ cycloalkyl, or —($C_7$-$C_{11}$)bicycloalkyl, wherein said alkyl optionally contains from one to five double bonds, and wherein each hydrogen atom of said alkyl is optionally replaced with a fluorine.

In another embodiment, the invention provides compounds of Formula I wherein A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl, —F, —Cl, —Br, and —$CF_3$; and $R^1$ is straight chain $C_2$-$C_{10}$ alkyl or branched $C_3$-$C_{10}$ alkyl.

In another embodiment, A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; R is selected from hydrogen, methyl, ethyl, —F, —Cl, —Br, and —$CF_3$; and $R^1$ is $C_3$-$C_{10}$ alkyl comprising a tertiary carbon, for example i-propyl or 2-methylpropyl, or $R^1$ is $C_4$-$C_{10}$ alkyl comprising a quaternary carbon, for example t-butyl.

In a further embodiment, A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl, —F, —Cl, —Br, and —$CF_3$; and $R^1$ is selected from phenyl, thienyl, and pyridyl, optionally and independently substituted with one or two substituents $R^{1b}$, preferably independently selected from —$C_1$-$C_4$ alkyl, $CF_3$, —$C_1$-$C_4$ alkyoxy, —F, —Cl, —Br, phenyl, and phenoxy.

In a further embodiment, A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl, —F, —Cl, —Br, and —$CF_3$; and $R^1$ is phenyl or pyridyl and is optionally substituted with one or two substituents $R^{1b}$ independently selected from —F, —Cl and, —$CF_3$.

In another embodiment, A is —C(=O)Z— or —C(=O)C(=O)—; Z is —$CH_2$— or —CH(OH)—; $R^3$ is $C_1$-$C_4$ alkyl wherein each hydrogen is independently optionally replaced with a fluorine, or $R^3$ is allyl or —$CH_2CH_2SCH_3$; $R^6$ is selected from hydrogen, methyl, ethyl, —F, —Cl, —Br, and —$CF_3$; and $R^1$ is $C_3$-$C_7$ cycloalkyl, for example [2.2.1]-heptanyl.

In another embodiment, this invention provides compounds of Formula I wherein $R^7$ is selected from —H, —$C_1$-$C_{12}$ alkyl optionally containing from one to five double bonds and wherein each hydrogen is independently optionally replaced with a fluorine, —$C_1$-$C_{20}$ alkoxy optionally containing from one to five double bonds and wherein each hydrogen is independently optionally replaced with a fluorine, —F, —Cl, —Br, —I, —CN, —$NO_2$, —($C_3$-$C_{12}$) cycloalkyl optionally substituted with from one to six fluorine, -((3-12 membered) heterocycloalkyl) optionally substituted with from one to six fluorine, —($C_6$-$C_{14}$) aryl, -((5-15 membered) heteroaryl), —CHO, —C(=O)($C_1$-$C_{15}$ alkyl), —C(=O)((5-12 membered)heterocycloalkyl), —C(=O)($C_6$-$C_{14}$ aryl), —C(=O)((5-15 membered) heteroaryl), —C(=O)($C_5$-$C_{12}$ cycloalkyl), —C(=O)O($C_1$-$C_8$ alkyl), —C(=O)N($C_1$-$C_{10}$ alkyl)($C_1$-$C_{10}$ alkyl), —C(=O)N($C_1$-$C_{10}$ alkyl)($C_6$-$C_{10}$ aryl), —C(=O)NH($C_6$-$C_{10}$ aryl), —C(=O)N($C_1$-$C_{10}$ alkyl)((5-10 membered) heteroaryl), —C(=O)NH((5-10 membered) heteroaryl), —C(=O)N($C_1$-$C_{10}$ alkyl)((5-10 membered) heterocycloalkyl), —C(=O)NH((5-10 membered) heterocycloalkyl), —C(=O)N($C_1$-$C_{10}$ alkyl)($C_5$-$C_{10}$ cycloalkyl), —C(=O)NH($C_5$-$C_{10}$ cycloalkyl), —S(O)$_n$,($C_1$-$C_{15}$ alkyl), —S(O)$_n$($C_5$-$C_{12}$ cycloalkyl), —S(O)$_n$,($C_6$-$C_{15}$ aryl), —S(O)$_n$((5-10 membered) heteroaryl), wherein said alkyl, cycloalkyl, heterocycloalkyl, aryl and heteroaryl are each optionally substituted with from one to three substituents independently selected from —F, —Cl, —Br, —I, —OH, —$C_1$-$C_6$ alkoxy independently optionally containing from one to three double or triple bonds, —$NR^9R^{10}$, —$(CH_2)_{1-10}NR^9R^{10}$, —$C(=O)R^{11}$, —$S(O)_nR^{11}$, —C(=O)$OR^{11}$, —$C(=O)NR^9R^{10}$, —$S(O)_nNR^9R^{10}$ —($C_3$-$C_{12}$) cycloalkyl, -((4-12 membered) heterocycloalkyl), —($C_6$-$C_{15}$) aryl, -((5-15 membered) heteroaryl), -((4-12 membered) heterocycloalkoxy), —($C_6$-$C_{12}$) aryloxy and -((6-12 membered) heteroaryloxy).

In another embodiment, $R^7$ is selected from —$C_1$-$C_{12}$ alkyl optionally containing from one to five double bonds and wherein each hydrogen is independently optionally replaced with a fluorine, —($C_3$-$C_{12}$) cycloalkyl optionally substituted with from one to six fluorine and -((3-12 membered) heterocycloalkyl) optionally substituted with from one to six fluorine, wherein said alkyl, cycloalkyl and heterocycloalkyl are each optionally substituted with from one to three substitutents independently selected from —OH, —$C_1$-$C_6$ alkoxy independently optionally containing from one to three double or triple bonds, —$NR^9R^{10}$, —$(CH_2)_{1-6}NR^9R^{10}$, —$C(=O)R^{11}$, —$C(=O)OR^{11}$, —$C(=O)NR^9R^{10}$, —$S(O)_nNR^9R^{10}$, —($C_6$-$C_{14}$) aryl, -((5-15 membered) heteroaryl), -((4-12 membered) heterocycloalkoxy), —($C_6$-$C_{12}$) aryloxy and -((6-12 membered) heteroaryloxy).

In another embodiment, the invention provides compounds of Formula I wherein $R^7$ is selected from —$C_1$-$C_{12}$ alkyl optionally containing from one to five double bonds, —($C_3$-$C_{12}$) cycloalkyl and -((3-12 membered) heterocycloalkyl), wherein said alkyl, cycloalkyl and heterocycloalkyl ar6 each optionally substituted with from one to three substitutents independently selected from —OH, —$C_1$-$C_6$ alkoxy independently optionally containing from one to three double or triple bonds, —$NR^9R^{10}$, and —$(CH_2)_{1-6}NR^9R^{10}$.

In another embodiment, $R^7$ is selected from —$C_1$-$C_{12}$ alkyl optionally containing from one to five double bonds, —$(C_3$-$C_{12})$ cycloalkyl and -(3-12 membered) heterocycloalkyl, wherein said alkyl, cycloalkyl and heterocycloalkyl are each optionally substituted with from one to three substitutents independently selected from —OH and -$C_1$-$C_6$ alkoxy independently optionally containing from one to three double or triple bonds.

In another embodiment, $R^7$ is selected from —$C_1$-$C_{12}$ alkyl optionally containing from one to five double bonds and -$C_3$-$C_{15}$ cycloalkyl, wherein said alkyl and cycloalkyl are each optionally independently substituted with from one to three substitutents —$NR^9R^{10}$.

In another embodiment, $R^7$ is -((3-12 membered) heterocycloalkyl), wherein said heterocycloalkyl is optionally substituted with from one to three substitutents independently selected from —OH, —$C_1$-$C_6$ alkyl independently optionally containing from one to three double or triple bonds, —$C_1$-$C_6$ alkoxy independently optionally containing from one to three double or triple bonds, —$(C_6$-$C_{10})$ aryl, and -(5-15 membered) heteroaryl.

The terms "halogen", "halo", and the like, as used herein, unless otherwise indicated, include F, Cl, Br, and I.

The term "alkyl", as used herein, unless otherwise indicated, includes saturated monovalent hydrocarbon radicals having straight or branched moieties. Examples of alkyl groups include, but are not limited to, methyl, ethyl, n-propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond-wherein alkyl is as defined above. Examples of alkynyl groups include, but are not limited to, ethynyl and 2-propynyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" and "tricycloalkyl" groups are non-aromatic saturated carbocyclic groups consisting of two or three rings respectively, wherein said rings share at least one carbon atom. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro[4.4]nonyl, spiro[4.3]octyl, and spiro[4.2]heptyl. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein. "Cycloalkenyl", "bicycloalkenyl", and "triccyloalkenyl" refer to non-aromatic carbocyclic cycloalkyl, bicycloalkyl, and tricycloalkyl moieties as defined above, except comprising one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl, and a non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl, and norcamphoryl. Other cycloalkenyl, bicycloalkenyl, and tricycloalkenyl groups are known in the art, and such groups are included within the definitions "cycloalkenyl", "bicycloalkenyl" and "tricycloalkenyl" herein.

The term "aryl", as used herein, unless otherwise indicated, includes an organic radical derived from an aromatic hydrocarbon by removal of one hydrogen, such as phenyl, naphthyl, indenyl, indanyl, and fluorenyl. "Aryl" encompasses fused ring groups wherein at least one ring is aromatic.

The terms "heterocyclic", "heterocycloalkyl", and like terms, as used herein, refer to non-aromatic cyclic groups containing one or more heteroatoms, prefereably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. In one embodiment, each ring in the heterobicycloalkyl contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

"Heteroaryl", as used herein, refers to aromatic groups containing one or more heteroat6ms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

Compounds of Formula I may have optical centers and therefore may occur in different enantiomeric, diastereomeric and meso configurations. The invention includes all enantiomers, diastereomers, and other stereoisomers of such compounds of Formula I, as well as racemic and other mixtures thereof. The invention also includes all tautomers of Formula I. When the compounds of Formula I of the present invention contain an optical center where $R^3$ and $R^4$ are attached, the "S" enantiomer is preferred.

The subject invention also includes isotopically-labeled compounds of Formula I, which are identical to those recited in Formula I, but for the fact that one or more atoms are replaced by an atom having an atomic mass or mass number different from the atomic mass or mass number most abundant in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of Formula I of the present invention and pharmaceutically acceptable salts, complexes and derivatives of said compounds that contain the aforementioned isotopes and/or other isotopes of other atoms are within the scope of this invention. Isotopically-labeled compounds of Formula I, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention can generally be prepared by substituting a readily available isotopically labeled reagent for a non-isotopically labeled reagent in the preparation of said compounds.

Salts of compounds of Formula I can be obtained by forming salts with any acidic or basic group present on a compound of Formula I. Examples of pharmaceutically acceptable salts of the compounds of Formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium.

Preferred embodiments of this invention include the following compounds of Formula I, all pharmaceutically acceptable salts thereof, complexes thereof, and derivatives thereof which convert into a pharmaceutically active compound upon administration:

2-(2-benzo[b]thiophen-4-yl-acetylamino)-N-(5-phenyl-2H-pyrazol-3-yl)-propionamide;
N-(5-phenyl-2H-pyrazol-3-yl)-2-(2-thiophen-2-yl-acetylamino)-propionamide;
2-[2-(4-fluoro-phenyl)-2-hydroxy-acetylamino]-N-(5-phenyl-2H-pyrazol-3-yl)-propionamide;
2-[2-(4-chloro-phenyl)-2-hydroxy-acetylamino]-N-(5-phenyl-2H-pyrazol-3-yl)-propionamide;
N-(5-phenyl-2H-pyrazol-3-yl)-2-(2-m-tolyl-acetylamino)-propionamide;
2-[2-(2,5-difluoro-phenyl)-acetylamino]-N-(5-phenyl-2H-pyrazol-3-yl)-propionamide;
2-[2-hydroxy-2-(4-trifluoromethyl-phenyl)-acetylamino]-N-(5-phenyl-2H-pyrazol-3-yl)-propionamide;
2-(2-fluoro-2-phenyl-acetylamino)-N-(5-phenyl-2H-pyrazol-3-yl)-propionamide;
N-(5-phenyl-2H-pyrazol-3-yl)-2-[2-(4-trifluoromethyl-phenyl)-acetylamino]-propionamide;
2-[2-(2-fluoro-5-trifluoromethyl-phenyl)-acetylamino]-N-(5-phenyl-2H-pyrazol-3-yl)-propionamide;
2-[2-(4-fluoro-3-trifluoromethyl-phenyl)-acetylamino]-N-(5-phenyl-2H-pyrazol-3-yl)-propionamide;
N-(5-phenyl-2H-pyrazol-3-yl)-2-[2-(2-trifluoromethoxy-phenyl)-acetylamino]-propionamide;
2-[2-(3-phenoxy-phenyl)-acetylamino]-N-(5-phenyl-2H-pyrazol-3-yl)-propionamide;
N-(5-phenyl-2,H-pyrazol-3-yl)-2-[2-(4-trifluoromethoxy-phenyl)-acetylamino]-propionamide;
2-[2-(3,5-difluoro-phenyl)-2-hydroxy-acetylamino]-N-(5-phenyl-2H-pyrazol-3-yl)-propionamide;
acetic acid (3,5-difluoro-phenyl)-[1-(5-phenyl-2H-pyrazol-3-ylcarbamoyl)-thylcarbamoyl]-methyl ester;
2-[2-(3,5-difuoro-phenyl)-2-hydroxy-acetylamino]-N-(5-phenyl-2H-pyrazol-3-yl)-propionamide;
2-[2-(3,5-difluoro-phenyl)-2-hydroxy-acetylamino]-N-(5-phenyl-2H-pyrazol-3-yl)-propionamide;
2-[2-(3,5-difluoro-phenyl)-2-hydroxy-acetylamino]-N-(5-phenyl-2H-pyrazol-3-yl)-butyramide;
2-[2-(3,5-difluoro-phenyl)-2-hydroxy-acetylamino]-N-(5-phenyl-2H-pyrazol-3-yl)-butyramide;
N-(5-phenyl-2H-pyrazol-3-yl)-2-(2-pyridin-3-yl-acetylamino)-butyramide;
N-(5-phenyl-2H-pyrazol-3-yl)-2-(2-pyridin-2-yl-acetylamino)-butyramide;
2-[2-(5-bromo-pyridin-3-yl)-acetylamino]-N-(5-phenyl-2H-pyrazol-3-yl)-butyramide;
2-(3-cyclopentyl-propionylamino)-N-(5-phenyl 2H-pyrazol-3-yl)-butyramide;
2-phenyl-cyclopropanecarboxylic acid [1-(5-phenyl-2H-pyrazol-3-ylcarbamoyl)-propyl]-amide;
N-[1-(5-phenyl-2H-pyrazol-3-ylcarbamoyl)-propyl]-succinamic acid methyl ester;
3,3-dimethyl-N-[1-(5-phenyl-2H-pyrazol-3-ylcarbamoyl)-propyl]-butyramide;
dodecanoic acid [1-(5-phenyl-2H-pyrazol-3-ylcarbamoyl)-propyl]-amide;
2-phenylacetylamino-N-(5-phenyl-2H-pyrazol-3-yl)-butyramide;
hexanoic acid [1-(5-phenyl-2H-pyrazol-3-ylcarbamoyl)-propyl]-amide;
heptanoic acid [1-(5-phenyl-2H-pyrazol-3-ylcarbamoyl)-propyl]-amide;
2-(3-chloro-propionylamino)-N-(5-phenyl-2H-pyrazol-3-yl)-butyramide;
2-(3-phenyl-propionylamino)-N-(5-phenyl-2H-pyrazol-3-yl)-butyramide;
3-methyl-N-[1-(5-phenyl-2H-pyrazol-3-ylcarbamoyl)-propyl]-butyramide;
decanoic acid [1-(5-phenyl-2H-pyrazol-3-ylcarbamoyl)-propyl]-amide;
2-butyrylamino-N-(5-phenyl-2H-pyrazol-3-yl)-butyramide;
5-chloro-pentanoic acid [1-(5-phenyl-2H-pyrazol-3-ylcarbamoyl)-propyl]-amide;
2-[2-(3-phenoxy-phenyl)-acetylamino]-N-(5-phenyl-2H-pyrazol-3-yl)-butyramide;
3-{[1-(5-phenyl-2H-pyrazol-3-ylcarbamoyl)-propylcarbamoyl]-methyl}-piperidine-1-carboxylic acid tert-butyl ester;
N-(5-phenyl-2H-pyrazol-3-yl)-2-[2-(3-trifluoromethyl-phenyl)-acetylamino]-butyramide;
2-[2-(3-iodo-phenyl)-acetylamino]-N-(5-phenyl-2H-pyrazol-3-yl)-butyramide;

2-[2-(3-chloro-phenyl)-acetylamino]-N-(5-phenyl-2H-pyrazol-3-yl)-butyramide;

4-methylsulfanyl-2-[2-(3-phenoxy-phenyl)-acetylamino]-N-(5-phenyl-2H-pyrazol-3-yl)-butyramide;

2-hydroxy-4-methyl-pentanoic acid [3-methylsulfanyl-1-(5-phenyl-2H-pyrazol-3-ylcarbamoyl)-propyl]-amide;

2-[2-(3,5-difluoro-phenyl)-2-hydroxy-acetylamino]-4-methylsulfanyl-N-(5-phenyl-2H-pyrazol-3-yl)-butyramide;

2-acetylamino-4-methylsulfanyl-N-(5-phenyl-2H-pyrazol-3-yl)- butyramide;

5-{2-[2-(3,5-difluoro-phenyl)-acetylamino]-butyrylamino}-1H-pyrazole-3-carboxylic acid ethyl ester;

5-[2-(2-hydroxy-4-methyl-pentanoylamino)-butyrylamino]-1H-pyrazole-3-carboxylic acid ethyl ester;

5-{2-[2-(3,5-difluoro-phenyl)-2-hydroxy-acetylamino]-butyrylamino}-1H-pyrazole-3-carboxylic acid ethyl ester;

2-[2-(3,5-difluoro-phenyl)-acetylamino]-N-(5-hydroxymethyl-2H-pyrazol-3-yl)-butyramide;

2-[2-(3,5-difluoro-phenyl)-acetylamino]-N-(5-hydrazinocarbonyl-2H-pyrazol-3-yl)-butyramide;

2-[2-(3,5-difluoro-phenyl)-acetylamino]-N-[5-(5-phenyl-4H-[1,2,4]triazol-3-yl)-2H-pyrazol-3-yl]-butyramide;

2-[2-(3,5-difluoro-phenyl)-acetylamino]-N-(4-oxo-4,5-dihydro-pyrazolo[1,5-d][1,2,4]triazin-2-yl)-butyramide;

2-[2-(3,5-difluoro-phenyl)-acetylamino]-N-(4-methoxy-7-phenyl-pyrazolo[1,5-d][1,2,4]triazin-2-yl)-butyramide;

5-{2-[2-(3,5-difluoro-phenyl)-acetylamino]-butyrylamino}-1H-pyrazole-3-carboxylic acid amide;

2-[2-(3,5-difluoro-phenyl)-acetylamino]-N-(4-oxo-7-phenylsulfanylmethyl-4,5-dihydro-pyrazolo[1,5-d][1,2,4]triazin-2-yl)-butyramide;

5-{2-[2-(3,5-difluoro-phenyl)-acetylamino]-butyrylamino}-1H-pyrazole-3-carboxylic acid methylamide;

5-{2-[2-(3,5-difluoro-phenyl)-acetylamino]-butyrylamino}-1H-pyrazole-3-carboxylic acid (1-ethyl-propyl)-amide;

5-{2-[2-(3,5-difluoro-phenyl)-acetylamino]-butyrylamino}-1H-pyrazole-3-carboxylic acid butyl-ethyl-amide;

5-{2-[2-(3,5-difluoro-phenyl)-acetylamino]-butyrylamino}-1H-pyrazole-3-carboxylic acid cyclopropylmethyl-amide;

2-[2-(3,5-difluoro-phenyl)-acetylamino]-N-[5-(morpholine-4-carbonyl)-2H-pyrazol-3-yl]-butyramide;

2-[2-(3,5-difluoro-phenyl)-acetylamino]-N-[5-(pyrrolidine-1-carbonyl)-2H-pyrazol-3-yl]-butyramide;

5-{2-[2-(3,5-difluoro-phenyl)-acetylamino]-butyrylamino}-1H-pyrazole-3-carboxylic acid piperidin-1-ylamide;

5-{2-[2-(3,5-difluoro-phenyl)-acetylamino]-butyrylamino}-1H-pyrazole-3-carboxylic acid sec-butyl-amide;

5-{2-[2-(3,5-difluoro-phenyl)-acetylamino]-butyrylamino}-1H-pyrazole-3-carboxylic acid ethyl-(2-hydroxy-ethyl)-amide;

5-{2-[2-(3,5-difluoro-phenyl)-acetylamino]-butyrylamino}-1H-pyrazole-3-carboxylic acid cyclohexyl-ethyl-amide;

5-{2-[2-(3,5-difluoro-phenyl)-acetylamino]-butyrylamino}-1H-pyrazole-3-carboxylic acid diallylamide;

2-[2-(3,5-difluoro-phenyl)-acetylamino]-N-(5-phenyl-2H-pyrazol-3-yl)-propionamide;

2-[2-(3,5-difluoro-phenyl)-acetylamino]-3-methyl-pentanoic acid (5-phenyl-2H-pyrazol-3-yl)-amide;

2-[2-(3,5-difluoro-phenyl)-acetylamino]-3-methyl-pentanoic acid (5-butyl-2H-pyrazol-3-yl)-amide;

2-phenylacetylamino-N-(5-phenyl-2H-pyrazol-3-yl)-propionamide;

2-[2-(3-fluoro-phenyl)-acetylamino]-N-(5-phenyl-2H-pyrazol-3-yl)-propionamide;

2-[2-(3,5-bis-trifluoromethyl-phenyl)-acetylamino]-N-(5-phenyl-2H-pyrazol-3-yl)-propionamide;

5-{2-[2-(3,5-difluoro-phenyl)-acetylamino]-propionylamino}-1H-pyrazole-3-carboxylic acid butyl ester;

2-[2-(3,5-difluoro-phenyl)-acetylamino]-N-[5-(1H-indol-3-yl)-2H-pyrazol-3-yl]-propionamide;

N-[5-(4-tert-butyl-phenyl)-2H-pyrazol-3-yl]-2-[2-(3,5-difluoro-phenyl)-acetylamino]-propionamide;

2-[2=(3,5-difluoro-phenyl)-acetylamino]-N-[5-(4-ethyl-phenyl)-2tH-pyrazol-3-yl]-propionamide;

5-{2-[2-(3,5-difluoro-phenyl)-acetylamino]-propionylamino}-1H-pyrazole-3-carboxylic acid ethyl ester;

N-(4-bromo-5-phenyl-2H-pyrazol-3-yl)-2-[2-(3,5-difluoro-phenyl)-acetylamino]-propionamide;

1-[2-(3,5-difluoro-phenyl)-acetylamino]-cyclopentanecarboxylic acid (5-phenyl-2H-pyrazol-3-yl)-amide;

N-(4-Chloro-5-phenyl-2H-pyrazol-3-yl)-2-[2-(3,5-difluoro-phenyl)-acetylamino]-propionamide;

2-[2-(3,5-difluoro-phenyl)-acetylamino]-pent-4-enoic acid (5-phenyl-2H-pyrazol-3-yl)-amide;

[(5-{2-[2-(3,5-difluoro-phenyl)-acetylamino]-propionylamino}-1H-pyrazole-3-carbonyl)-amino]-phenyl-acetic acid tert-butyl ester;

5-{2-[2-(3,5-difluoro-phenyl)-acetylamino]-propionylamino}-1H-pyrazole-3-carboxylic acid benzylamide;

2-[2-(3,5-difluoro-phenyl)-acetylamino]-pent-4-enoic acid (4-bromo-5-phenyl-2H-pyrazol-3-yl)-amide;

5-{2-[2-(3,5-difluoro-phenyl)-acetylamino]-propionylamino}-1H- pyrazole-3-carboxylic acid methyl ester;

2-[2-(3,5-difluoro-phenyl)-acetylamino]-2-phenyl-N-(5-phenyl-2H-pyrazol-3-yl)-acetamide;

2-[2-(3,5-difluoro-phenyl)-2-hydroxy-acetylamino]-pent-4-enoic acid (5-phenyl-2H-pyrazol-3-yl)-amide;

3-[2-(3,5-difluoro-phenyl)-2-hydroxy-acetylamino]-N-(5-phenyl-2H-pyrazol-3-yl)-succinamic acid methyl ester;

2-cyclohexyl-2-[2-(3,5-difluoro-phenyl)-acetylamino]-N-(5-phenyl-2H-pyrazol-3-yl)-acetamide;

2-cyclohexyl-2-[2-(3,5-difluoro-phenyl)-2-hydroxy-acetylamino]-N-(5-phenyl-2H-pyrazol-3-yl)-acetamide;

3-[2-(3,5-difluoro-phenyl)-2-hydroxy-acetylamino]-N-(5-phenyl-2H- pyrazol-3-yl)-succinamic acid benzyl ester;

2-(2-hydroxy-2-phenyl-acetylamino)-pent-4-enoic acid (5-thiophen-2-yl-2H-pyrazol-3-yl)-amide;

2-[2-(3,5-difluoro-phenyl)-acetylamino]-pentanoic acid (5-methyl-1-phenyl-1H-pyrazol-3-yl)-amide;

2-(2-bicyclo[2 .2.1 ]hept-2-yl-acetylamino)-pentanoic acid (5-phenyl-2H-pyrazol-3-yl)-amide;

2-(2-cyclohexyl-acetylamino)-pentanoic acid (5-phenyl-2H-pyrazol-3- yl)-amide;

2-(3-hydroxy-2-phenyl-propionylamino)-pentanoic acid (5-phenyl-2H-pyrazol-3-yl)-amide;

2-(2-adamantan-1-yl-acetylamino)-pentanoic acid (5-phenyl-2H-pyrazol-3-yl)-amide;

4-methyl-pentanoic acid [1-(5-phenyl-2H-pyrazol-3-ylcarbamoyl)- butyl]-amide;

3-methyl-pentanoic acid [1-(5-phenyl-2H-pyrazol-3-ylcarbamoyl)-butyl]-amide;

2-(2-cyclopentyl-acetylamino)-pentanoic acid (5-phenyl-2H-pyrazol-3-yl)- amide;

.2-(2-cyclopropyl-acetylamino)-pentanoic acid (5-phenyl-2H-pyrazol-3-yl)-amide;

2-(2-indan-2-yl-acetylamino)-pentanoic acid (5-phenyl-2H-pyrazol-3-yl)-amide;

2-(3-phenyl-butyrylamino)-pentanoic acid (5-phenyl-2H-pyrazol-3-yl)-amide;

5-oxo-hexanoic acid [1-(5-phenyl-2H-pyrazol-3-ylcarbamoyl)-butyl]-amide;

2-[2-(3-chloro-phenyl)-acetylamino]-pentanoic acid (5-phenyl-2H-pyrazol-3-yl)-amide;

2-[2-(3-bromo-phenyl)-acetylamino]-pentanoic acid (5-phenyl-2H-pyrazol-3-yl)-amide;

2-[2-(3,5-difluoro-phenyl)-acetylamino]-N-(5-furan-2-yl-2H-pyrazol-3-yl)-propionamide;

N-(5-tert-butyl-2H-pyrazol-3-yl)-2-[2-(3,5-difluoro-phenyl)-acetylamino]-propionamide;

N-(5-cyclopropyl-2H-pyrazol-3-yl)-2-[2-(3,5-difluoro-phenyl)-acetylamino]-propionamide;

2-[2-(3,5-difluoro-phenyl)-acetylamino]-pentanoic acid (5-furan-2-yl-2H-pyrazol-3-yl)-amide;

2-[2-(3,5-difluoro-phenyl)-acetylamino]-pentanoic acid (5-thiophen-2-yl-2H-pyrazol-3-yl)-amide;

2-[2-(3,5-difluoro-phenyl)-acetylamino]-pentanoic acid (5-tert-butyl-2H-pyrazol-3-yl)-amide;

2-[2-(3,5-difluoro-phenyl)-acetylamino]-pentanoic acid [5-(4-chloro-phenyl)-2H-pyrazol-3-yl]-amide;

N-(5-tert-butyl-2H-pyrazol-3-yl)-2-[2-(3,5-difluoro-phenyl)-acetylamino]-3-methyl-butyramide;

1-[2-(3,5-difluoro-phenyl)-acetylamino]-cyclopropanecarboxylic acid (5-tert-butyl-2H-pyrazol-3-yl)-amide;

1-[2-(3,5-difluoro-phenyl)-acetylamino]-cyclopropanecarboxylic acid (5-furan-2-yl-2H-pyrazol-3-yl)-amide;

N-(5-biphenyl-4-yl-2H-pyrazol-3-yl)-2-[2-(3,5-difluoro-phenyl)-acetylamino]-propionamide;

2-[2-(3,5-difluoro-phenyl)-acetylamino]-N-[5-(3',4'-dimethyl-biphenyl-4-yl)-2H-pyrazol-3-yl]-propionamide;

2-[2-(3,5-difluoro-phenyl)-acetylamino]-pentanoic acid (5-phenyl-2H-pyrazol-3-yl)-amide;

2-phenylmethanesulfonylamino-N-(5-phenyl-2H-pyrazol-3-yl)-propionamide;

2-(4-fluoro-phenylmethanesulfonylamino)-N-(5-phenyl-2H-pyrazol-3-yl)-propionamide;

2-(2-nitro-phenylmethanesulfonylamino)-N-(5-phenyl-2H-pyrazol-3-yl)-propionamide;

2-phenylmethanesulfonylamino-pentanoic acid (5-tert-butyl-2H-pyrazol-3-yl)-amide;

2-(4-fluoro-phenylmethanesulfonylamino)-pentanoic acid (5-tert-butyl-2H-pyrazol-3-yl)-amide;

N-(5-tert-butyl-2H-pyrazol-3-yl)-2-phenylmethanesulfonylamino-propionamide;

2-p-tolylmethanesulfonylamino-pentanoic acid (5-tert-butyl-2H-pyrazol-3-yl)-amide;

2-phenylmethanesulfonylamino-pentanoic acid (5-phenyl-2H-pyrazol-3-yl)-amide;

2-(decane-1-sulfonylamino)-pentanoic acid (5-phenyl-2H-pyrazol-3-yl)-amide;

2-(biphenyl-4-sulfonylamino)-pentanoic acid (5-phenyl-2H-pyrazol-3-yl)-amide;

2-(4-chloro-phenylmethanesulfonylamino)-pentanoic acid (5-phenyl-2H-pyrazol-3-yl)-amide;

2-benzenesulfonylamino-4-methylsulfanyl-N-(5-phenyl-2H-pyrazol-3-yl)-butyramide;

2-(4-fluoro-phenylmethanesulfonylamino)-pentanoic acid (5-phenyl-2H-pyrazol-3-yl)-amide;

2-(4,5-dichloro-thiophene-2-sulfonylamino)-4-methylsulfanyl-N-(5-phenyl-9H-pyrazol-3-yl)-butyramide; and 2-(4-chloro-phenylmethanesulfonylamino)-pentanoic acid (5-tert-butyl-2H-pyrazol-3-yl)-amide.

Other specific compounds of Formula I of the invention are:

2-[2-(3,5-difluoro-phenyl)-acetylamino]-N-[5-(5-methoxy-1,5-dimethyl-hexyl)-2H-pyrazol-3-yl]-butyramide;

2-[2-(3,5-difluoro-phenyl)-2-hydroxy-acetylamino]-N-[5-(5-methoxy-1,5-dimethyl-hexyl)-2H-pyrazol-3-yl]-butyramide;

2-[2-(5-bromo-pyridin-3-yl)-2-hydroxy-acetylamino]-N-[5-(5-methoxy-1,5-dimethyl-hexyl)-2H-pyrazol-3-yl]-butyramide;

2-hydroxy-N-{1-[5-(5-methoxy-1,5-dimethyl-hexyl)-2H-pyrazol-3-ylcarbamoyl]-propyl}-3-methyl-butyramide;

2-hydroxy-N-{1-[5-(5-methoxy-1,5-dimethyl-hexyl)-2H-pyrazol-3-ylcarbamoyl]-propyl}-3,3-dimethyl-butyramide;

2-(4,5-dichloro-thiophene-2-sulfonylamino)-4-methylsulfanyl-N-(5-phenyl-2H-pyrazol-3-yl)-butyramide;

2-(4-chloro-phenylmethanesulfonylamino)-pentanoic acid (5-tert-butyl-2H-pyrazol-3-yl)-amide; and pharmaceutically acceptable salts thereof, complexes thereof, and derivatives thereof which convert into a pharmaceutically active compound upon administration.

Other preferred compounds of Formula I are:

5-{2-[2-(3,5-Difluoro-phenyl)-acetylamino]-butyrylamino}-1H-pyrazole-3-carboxylic acid benzyl-methyl-amide;

3,7-Dimethyl-oct-6-enoic acid [1-(5-phenyl-2H-pyrazol-3-ylcarbamoyl)-butyl]-amide;

2-[2-(1-Benzyl-piperidin-3-yl)-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid dibutylamide;

3-{[1-(5-Phenyl-2H-pyrazol-3-ylcarbamoyl)-propylcarbamoyl]-methyl}-piperidine-1-carboxylic acid tert-butyl ester;

3-{[1-(5-Phenyl-2H-pyrazol-3-ylcarbamoyl)-propylcarbamoyl]-methyl}-piperidine-1-carboxylic acid tert-butyl ester;

5-{2-[2-(3,5-Difluoro-phenyl)-acetylamino]-butyrylamino}-1H-pyrazole-3-carboxylic acid ethyl-methyl-amide;

2-[2-(3-Chloro-phenyl)-acetylamino]-pentanoic acid [5-(4-chloro-phenyl)-2H-pyrazol-3-yl]-amide;

2-[2-(3,5-Difluoro-phenyl)-acetylamino]-N-[5-(4-phenyl-piperazine-1-carbonyl)-2H-pyrazol-3-yl]-butyramide;

2-[2-(3,5-Difluoro-phenyl)-acetylamino]-N-[5-(2-hydroxymethyl-pyrrolidine-1-carbonyl)-2H-pyrazol-3-yl]-butyramide;

2-(2-Cyclohexyl-2-hydroxy-acetylamino)-pentanoic acid (5-phenyl-2H-pyrazol-3-yl)-amide;

2-(2-Cyclohexyl-2-hydroxy-acetylamino)-pentanoic acid (5-phenyl-2H-pyrazol-3-yl)-amide;

2-[2-(3,5-Difluoro-phenyl)-acetylamino]-N-[5-(2,6-dimethyl-morpholine-4-carbonyl)-2H-pyrazol-3-yl]-butyramide;

5-{2-[2-(3,5-Difluoro-phenyl)-acetylamino]-butyrylamino}-1H-pyrazole-3-carboxylic acid (2-hydroxy-ethyl)-propyl-amide;

1-(5-{2-[2-(3,5-Difluoro-phenyl)-acetylamino]-butyrylamino}-1H-pyrazole-3-carbonyl)-piperidine-3-carboxylic acid ethyl ester;

5-{2-[2-(3,5-Difluoro-phenyl)-acetylamino]-butyrylamino}-1H-pyrazole-3-carboxylic acid (2,2-dimethoxy-ethyl)-methyl-amide;

5-{2-[2-(3,5-Difluoro-phenyl)-acetylamino]-butyrylamino}-1H-pyrazole-3-carboxylic acid diethylamide;

5-{2-[2-(3,5-Difluoro-phenyl)-acetylamino]-butyrylamino}-1H-pyrazole-3-carboxylic acid diisobutylamide;

3,7-Dimethyl-oct-6-enoic acid [1-(5-phenyl-2H-pyrazol-3-ylcarbamoyl)-butyl]-amide;

3,7-Dimethyl-oct-6-enoic acid [1-(5-phenyl-2H-pyrazol-3-ylcarbamoyl)-butyl]-amide;

5-{2-[2-(3,5-Difluoro-phenyl)-acetylamino]-butyrylamino}-1H-pyrazole-3-carboxylic acid dibenzylamide;

2-[2-(3,5-Difluoro-phenyl)-acetylamino]-N-[5-(2-ethyl-piperidine-1-carbonyl)-2H-pyrazol-3-yl]-butyramide;

5-{2-[2-(3,5-Difluoro-phenyl)-acetylamino]-butyrylamino}-1H-pyrazole-3-carboxylic acid benzyl-ethyl-amide;

5-{2-[2-(3,5-Difluoro-phenyl)-acetylamino]-butyrylamino}-1H-pyrazole-3-carboxylic acid butyl-methyl-amide;

5-{2-[2-(3,5-Difluoro-phenyl)-acetylamino]-butyrylamino}-1H-pyrazole-3-carboxylic acid dihexylamide;

2-[2-(2,3-Difluoro-phenyl)-2-hydroxy-acetylamino]-pentanoic acid (5-phenyl-2H-pyrazol-3-yl)-amide;

2-[2-(1-Benzenesulfonyl-piperidin-3-yl)-acetylamino]-N-(5-phenyl-2H-pyrazol-3-yl)-butyramide;

2-[2-(1-Acetyl-piperid in-3-yl)-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid dipropylamide;

2-[2-(3,5-Difluoro-phenyl)-acetylamino]-N-[5-(1-methyl-1H-benzoimidazol-2-yl)-2H-pyrazol-3-yl]-butyramide;

2-[2-(5-Bromo-pyridin-3-yl)-acetylamino]-pentanoic acid [5-(4-chloro-phenyl)-2H-pyrazol-3-yl]-amide;

2-[2-(3-Trifluoromethyl-phenyl)-acetylamino]-pentanoic acid [5-(4-chloro-phenyl)-2H-pyrazol-3-yl]-amide;

2-[2-(3-Methoxy-phenyl)-acetylamino]-pentanoic acid [5-(4-chloro-phenyl)-2H-pyrazol-3-yl]-amide;

3-{1-[5-(4-Chloro-phenyl)-2H-pyrazol-3-ylcarbamoyl]-butylcarbamoyl}-5-methyl-2-propyl-hexanoic acid tert-butyl ester;

N-(5-Phenyl-2H-pyrazol-3-yl)-2-[2-(5-phenyl-pyridin-3-yl)-acetylamino]-butyramide;

E-224354: N-(5-Phenyl-2H-pyrazol-3-yl)-2-(2-piperidin-1-yl-acetylamino)-butyramide;

5-{2-[2-(3,5-Difluoro-phenyl)-acetylamino]-butyrylamino}-1H-pyrazole-3-carboxylic acid dipentylamide;

2Hydroxy-hexanoic acid [1-(5-phenyl-2H-pyrazol-3-yl-carbamoyl)-butyl]-amide;

2-[2-(2-Chloro-phenyl)-2-hydroxy-acetylamino]-pentanoic acid (5-phenyl-2H-pyrazol-3-yl)-amide;

2-[2-(3,5-Difluoro-phenyl)-acetylamino]-pentanoic acid (2H-pyrazol-3-yl)-amide;

2-[2-(3,5-Difluoro-phenyl)-acetylamino]-N-[5-(5,6,7,8-tetrahydro- [1,2,4]triazolo[4,3-a]pyridin-3-yl)-2H-pyrazol-3-yl]-butyramide;

2-[2-(3,5-Difluoro-phenyl)-acetylamino]-3,3-dimethyl-N-(5-phenyl-2H-pyrazol-3-yl)-butyramide;

2-(2-Hydroxy-3-methyl-butyrylamino)-pentanoic acid (5-phenyl-2H-pyrazol-3-yl)-amide;

2-[2-(5-o-Tolyl-pyridin-3-yl)-acetylamino]-pentanoic acid [5-(4-chloro-phenyl)-2H-pyrazol-3-yl]-amide;

2-Hydroxy-3-methyl-N-[1-(5-phenyl-2H-pyrazol-3-yl-carbamoyl)-propyl]-butyramide;

2-[2-(2-Oxo-azepan-3-yl)-acetylamino]-N-(5-phenyl-2H-pyrazol-3-yl)-butyramide;

2-[2-(2-Oxo-azepan-3-yl)-acetylamino]-N-(5-phenyl-2H-pyrazol-3-yl)-butyramide;

3,7-Dimethyl-octa-2,6-dienoic acid [1-(5-phenyl-2H-pyrazol-3-ylcarbamoyl)-butyl]-amide;

2-[2-(3,5-Difluoro-phenyl)-acetylamino]-pentanoic acid (5-methyl-2H-pyrazol-3-yl)-amide; and 2-[2-(3,5-Difluoro-phenyl)-acetylamino]-hexanoic acid (5-phenyl-2H-pyrazol-3-yl)-amide;

2-[2-(3,5-Difluoro-phenyl)-acetylamino]-N-(4-oxo-4,5-dihydro-pyrazolo[1,5-d][1,2,4]triazin-2-yl)-butyramide;

2-[2-(3,5-Difluoro-phenyl)-acetylamino]-N-(4-methoxy-7-phenyl-pyrazolo[1,5-d][1,2,4]triazin-2-yl)-butyramide;

2-[2-(3,5-Difluoro-phenyl)-acetylamino]-N-(4-oxo-7-phenylsulfanylmethyl-4,5-dihydro-pyrazolo[1,5-d][1,2,4]triazin-2-yl)-butyramide;

2-[2-(3,5-Difluoro-phenyl)-acetylamino]-pentanoic acid (5-methyl-1-phenyl-1H-pyrazol-3-yl)-amide; and pharmaceutically acceptable salts thereof, complexes thereof, and derivatives thereof which convert into a pharmaceutically-active compound-upon administration.

The most preferred embodiments of this invention include the following compounds of Formula I, all pharmaceutically acceptable salts thereof, complexes thereof, and derivatives thereof which convert into a pharmaceutically active compound upon administration:

2-[2-(3,5-Difluoro-phenyl)-acetylamino]-N-(5-furan-2-yl-2H-pyrazol-3-yl)-propionamide;

N-(5-tert-Butyl-2H-pyrazol-3-yl)-2-[2-(3,5-difluoro-phenyl)-acetylamino]-propionamide;

N-(5-Cyclopropyl-2H-pyrazol-3-yl)-2-[2-(3,5-difluoro-phenyl)-acetylamino]-propionamide;

2-[2-(3,5-Difluoro-phenyl)-acetylamino]-pentanoic acid (5-phenyl-2H-pyrazol-3-yl)-amide;

2-[2-(3,5-Difluoro-phenyl)-acetylamino]-pentanoic acid (5-phenyl-2H-pyrazol-3-yl)-amide;

2-[2-(3,5-Difluoro-phenyl)-acetylamino]-pentanoic acid (5-furan-2-yl-2H-pyrazol-3-yl)-amide;

2-[2-(3,5-Difluoro-phenyl)-acetylamino]-pentanoic acid (5-thiophen-2-yl-2H-pyrazol-3-yl)-amide;

2-[2-(3,5-Difluoro-phenyl)-acetylamino]-pentanoic acid (5-cyclopropyl-2H-pyrazol-3-yl)-amide;

2-[2-(3,5-Difluoro-phenyl)-acetylamino]-pentanoic acid [5-(4-chloro-phenyl)-2H-pyrazol-3-yl]-amide;

2-Phenylacetylamino-N-(5-phenyl-2H-pyrazol-3-yl)-propionamide;

2-[2-(3-Fluoro-phenyl)-acetylamino]-N-(5-phenyl-2H-pyrazol-3-yl)-propionamide;

2-[2-(3,5-Difluoro-phenyl)-2-hydroxy-acetylamino]-N-(5-phenyl-2H-pyrazol-3-yl)-propionamide;

2-[2-(4-Fluoro-3-trifluoromethyl-phenyl)-acetylamino]-N-(5-phenyl-2H-pyrazol-3-yl)-propionamide;

2-[2-(3-Phenoxy-phenyl)-acetylamino]-N-(5-phenyl-2H-pyrazol-3-yl)-propionamide;

2-[2-(3,5-Difluoro-phenyl)-acetylamino]-pent-4-enoic acid (5-phenyl-2H-pyrazol-3-yl)-amide;

2-[2-(3,5-Difluoro-phenyl)-2-hydroxy-acetylamino]-4-methylsulfanyl-N- (5-phenyl-2H-pyrazol-3-yl)-butyramide;

2-[2-(3,5-Difluoro-phenyl)-2-hydroxy-acetylamino]-N-(5-phenyl-2H-pyrazol-3-yl)-butyramide;

2-[2-(3,5-Difluoro-phenyl)-2-hydroxy-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid ethyl ester;

5-[2-(2-Hydroxy-4-methyl-pentanoylamino)-butyrylamino]-1H-pyrazole-3-carboxylic acid ethyl ester;

5-{2-[2-(3,5-Difluoro-phenyl)-2-hydroxy-acetylamino]-butyrylamino}-1H-pyrazole-3-carboxylic acid ethyl ester;

2-[2-(3,5-Difluoro-phenyl)-2-hydroxy-acetylamino]-N-(5-phenyl-2H-pyrazol-3-yl)-propionamide;

N-(5-Phenyl-2H-pyrazol-3-yl)-2-(2-pyrid in-3-yl-acetylamino)-butyramide;

2-[2-(5-Bromo-pyridin-3-yl)-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid butyl-ethyl-amide;

2-[2-(3-Phenoxy-phenyl)-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid piperidin-1-ylamide;

5-{2-[2-(3,5-Difluoro-phenyl)-acetylamino]-butyrylamino}-1H-pyrazole-3-carboxylic acid cyclohexyl-ethyl-amide;

2-(2-Cyclohexyl-acetylamino)-pentanoic acid (5-phenyl-2H-pyrazol-3-yl)-amide;

4-Methyl-pentanoic acid [1-(5-phenyl-2H-pyrazol-3-ylcarbamoyl)-butyl]-amide;

3-Methyl-pentanoic acid [1-(5-phenyl-2H-pyrazol-3-ylcarbamoyl)-butyl]-amide;

2-(2-Cyclopentyl-acetylamino)-pentanoic acid (5-phenyl-2H-pyrazol-3-yl)-amide;

2-(2-Cyclopropyl-acetylamino)-pentanoic acid (5-phenyl-2H-pyrazol-3-yl)-amide;

2-[2-(3-Chloro-phenyl)-acetylamino]-pentanoic acid (5-phenyl-2H-pyrazol-3-yl)-amide;

2-[2-(3-Bromo-phenyl)-acetylamino]-pentanoic acid (5-phenyl-2H-pyrazol-3-yl)-amide;

5-{2-[2-(3,5-Difluoro-phenyl)-acetylamino]-butyrylamino}-1H-pyrazole-3-carboxylic acid benzyl-methyl-amide;

3,7-Dimethyl-oct-6-enoic acid [1-(5-phenyl-2H-pyrazol-3-ylcarbamoyl)-butyl]-amide;

5-{2-[2-(3,5-Difluoro-phenyl)-acetylamino]-butyrylamino}-1H-pyrazole-3-carboxylic acid dibutylamide;

5-{2-[2-(3,5-Difluoro-phenyl)-acetylamino]-butyrylamino}-1H-pyrazole-3-carboxylic acid ethyl-methyl-amide;

2-(2-Cyclohexyl-2-hydroxy-acetylamino)-pentanoic acid (5-phenyl-2H-pyrazol-3-yl)-amide;

2-[2-(3,5-Difluoro-phenyl)-acetylamino]-N-[5-(2,6-dimethyl-morpholine-4-carbonyl)-2H-pyrazol-3-yl]-butyramide;

5-{2-[2-(3,5-Difluoro-phenyl)-acetylamino]-butyrylamino}-1H-pyrazole-3-carboxylic acid (2-hydroxy-ethyl)-propyl-amide;

1-(5-{2-[2-(3,5-Difluoro-phenyl)-acetylamino]-butyrylamino}-1H-pyrazole-3-carbonyl)--piperidine-3-carboxylic acid ethyl ester;

5-{2-[2-(3,5-Difluoro-phenyl)-acetylamino]-butyrylamino}-1H-pyrazole-3-carboxylic acid (2,2-dimethoxy-ethyl)-methyl-amide;

5-{2-[2-(3,5-Difluoro-phenyl)-acetylamino]-butyrylamino}-1H-pyrazole-3-carboxylic acid diisobutylamide;

3,7-Dimethyl-oct-6-enoic acid [1-(5-phenyl-2H-pyrazol-3-ylcarbamoyl)-butyl]-amide;

5-{2-[2-(3,5-Difluoro-phenyl)-acetylamino]-butyrylamino}-1H-pyrazole-3-carboxylic acid dibenzylamide;

2-[2-(3,5-Difluoro-phenyl)-acetylamino]-N-[5-(2-ethyl-piperidine-1-carbonyl)-2H-pyrazol-3-yl]-butyramide;

5-{2-[2-(3,5-Difluoro-phenyl)-acetylamino]-butyrylamino}-1H-pyrazole-3-carboxylic acid benzyl-ethyl-amide;

5-{2-[2-(3,5-Difluoro-phenyl)-acetylamino]-butyrylamino}-1H-pyrazole-3-carboxylic acid butyl-methyl-amide;

5-{2-[2-(3,5-Difluoro-phenyl)-acetylamino]-butyrylamino}-1H-pyrazole-3-carboxylic acid dihexylamide;

2-[2-(2,3-Difluoro-phenyl)-2-hydroxy-acetylamino]-pentanoic acid (5-phenyl-2H-pyrazol-3-yl)-amide;

2-[2-(1-Acetyl-piperidin-3-yl)-acetylamino]-N-(5-phenyl-2H-pyrazol-3-yl)-butyramide;

5-{2-[2-(3,5-Difluoro-phenyl)-acetylamino]-butyrylamino}-1H-pyrazole-3-carboxylic acid dipropylamide;

N-(5-Phenyl-2H-pyrazol-3-yl)-2-[2-(5-phenyl-pyridin-3-yl)-acetylamino]-butyramide;

5-{2-[2-(3,5-Difluoro-phenyl)-acetylamino]-butyrylamino})1H-pyrazole-3-carboxylic acid dipentylamide;

2-[2-(5-o-Tolyl-pyridin-3-yl)-acetylamino]-pentanoic acid [5-(4-chloro-phenyl)-2H-pyrazol-3-yl]-amide; and 2-Hydroxy-3-methyl-N-[1-(5-phenyl-2H-pyrazol-3-yl-carbamoyl)-ethyl]-butyramide.

The present invention also provides a pharmaceutical composition for treating in a mammal a disease or condition associated with Aβ-peptide production, which pharmaceutical composition comprises a compound of Formula I in an amount effective in inhibiting gamma-secretase and a pharmaceutically acceptable carrier.

The present invention also provides a pharmaceutical composition for treating in a mammal, including in a human, a disease or condition associated with Aβ-peptide production, which pharmaceutical composition comprises a compound of Formula I in an amount effective in inhibiting Aβ-production and a pharmaceutically acceptable carrier.

The present invention also provides a pharmaceutical composition for treating in a mammal, including in a human, a disease or condition associated with Aβ-peptide production, which pharmaceutical composition comprises a compound of Formula I in an amount effective in inhibiting said disease or condition and a pharmaceutically acceptable carrier.

The present invention also provides a pharmaceutical composition for treating in a mammal, including in a human, a disease or condition selected from Alzheimer's disease, hereditary cerebral hemorrhage with amyloidosis of the Dutch type, cerebral amyloid angiopathy, systemic amyloidosis, a prion-mediated disease, inclusion body myositis, stroke, and Down's Syndrome, which pharmaceutical composition comprises a compound of Formula I in an amount effective in inhibiting Aβ-production and a pharmaceutically acceptable carrier.

The present invention also provides a pharmaceutical composition for treating in a mammal, including in a human, a disease or condition selected from Alzheimer's disease, hereditary cerebral hemorrhage with amyloidosis of the Dutch typecerebral amyloid angiopathy, systemic amytoidosis, a prion-mediated disease, inclusion body myositis, stroke, and Down's Syndrome, which pharmaceutical composition comprises a compound of Formula I in an amount effective in inhibiting said disease or condition and a pharmaceutically acceptable carrier.

The present invention also provides a method for treating in a mammal, including in a human, a disease or condition associated with Aβ-peptide production, which method comprises administering to said mammal an amount of a compound of Formula I effective in inhibiting Aβ-production.

The present invention also provides a method for treating in a mammal, including in a human, a disease or condition associated with Aβ-peptide production, which method comprises administering to said mammal an amount of a compound of Formula I effective in treating said disease or condition.

The present invention also provides a method for treating in a mammal, including in a human, a disease or condition selected from Alzheimer's disease, hereditary cerebral hemorrhage with amyloidosis of the Dutch type, cerebral amyloid angiopathy, systemic amyloidosis a prion-mediated disease, inclusion body myositis, stroke, and Down's Syndrome, which method comprises administering to said mammal an amount of a compound of Formula I effective in inhibiting Aβ-production.

The present invention also provides a method for treating in a mammal, including in a human, a disease or condition selected from Alzheimer's disease, hereditary cerebral hemorrhage with amyloidosis of the Dutch type, cerebral amyloid angiopathy, systemic amyloidosis, a prion-mediated disease, inclusion body myositis, stroke, and Down's Syndrome, which method comprises administering to said mammal an amount of a compound of Formula I effective in treating said disease or condition.

Compounds in Formula I may be used alone or used as a combination with any other drug, including, but not limited to, any memory enhancement agent, antidepressant agent, anxiolytic, antipsychotic agent, sleep disorder agent, anti-inflammatory agent, anti-oxidant agent, cholesterol modulating agent (for example, an agent that lowers LDL or increases HDL), or anti-hypertension agent. Accordingly, this invention also provides a pharmaceutical composition for treatment of a mammal, including a human, in need thereof comprising an effective amount of a compound of Formula I and an effective amount of another drug, for example a memory enhancement agent, antidepressant agent, anxiolytic, antipsychotic agent, sleep disorder agent, anti-inflammatory agent, anti-oxidant agent, cholesterol modulating agent (for example, an agent that lowers LDL or increases HDL),or anti-hypertension agent, and a pharmaceutically acceptable carrier. This invention also provides a method for treating dementia, for example Alzheimer's disease, in a mammal, including in a human, comprising administering to the mammal an effective amount of a compound of Formula I and an effective amount of another drug, for example a memory enhancement agent, antidepressant agent, anxiolytic, antipsychotic agent, sleep disorder agent, anti-inflammatory agent, anti-oxidant agent, cholesterol modulating agent (for example, an agent that lowers LDL or increases HDL),or anti-hypertension agent.

Compounds of Formula I, or any of the combinations described in the immediately preceding paragraph, may optionally be used in conjunction with a know β-glycoprotein inhibitor, such as verapamil.

References herein to diseases and conditions "associated with Aβ-peptide production" mean a disease or condition that is caused at least in part by Aβ-peptide and/or the production thereof. Thus, Aβ-peptide is a contributing factor, but not necessarily the only contributing factor, to "a disease or condition associated with Aβ-peptide production".

The terms "treatment", "treating", and the like, refer to reversing, alleviating, or inhibiting the progress of a disorder or condition. As used herein, "treatment" and "treating" and like terms can also refer to decreasing the probability or incidence of occurrence of a disease or condition in a mammal compared to an untreated control population, or in the same mammal prior to treatment, according to the present invention. "treatment" or "treating" can also include delaying or preventing the onset of a disease or condition. "Treatment" or "treating" as used herein also encompasses preventing the recurrence of disease or condition.

In the present invention the pyrazole ring is always aromatic. To those skilled in the art it is well understood that the pyrazole ring is aromatic when $R^8$ is attached to either of the ring nitrogen atoms.

It is also well known that when $R^8$ is hydrogen, two tautomeric forms of formula I exist in solution equilibrium.

DETAILED DESCRIPTION OF THE INVENTION

Compounds of Formula I may be prepared according to the following reaction Schemes and discussion. Unless otherwise indicated, $R^1$, $R^2$, $R^3$, $R^4$, $R^5$, $R^6$, $R^7$, $R^8$ and A in the reaction schemes and discussion that follows are as defined above.

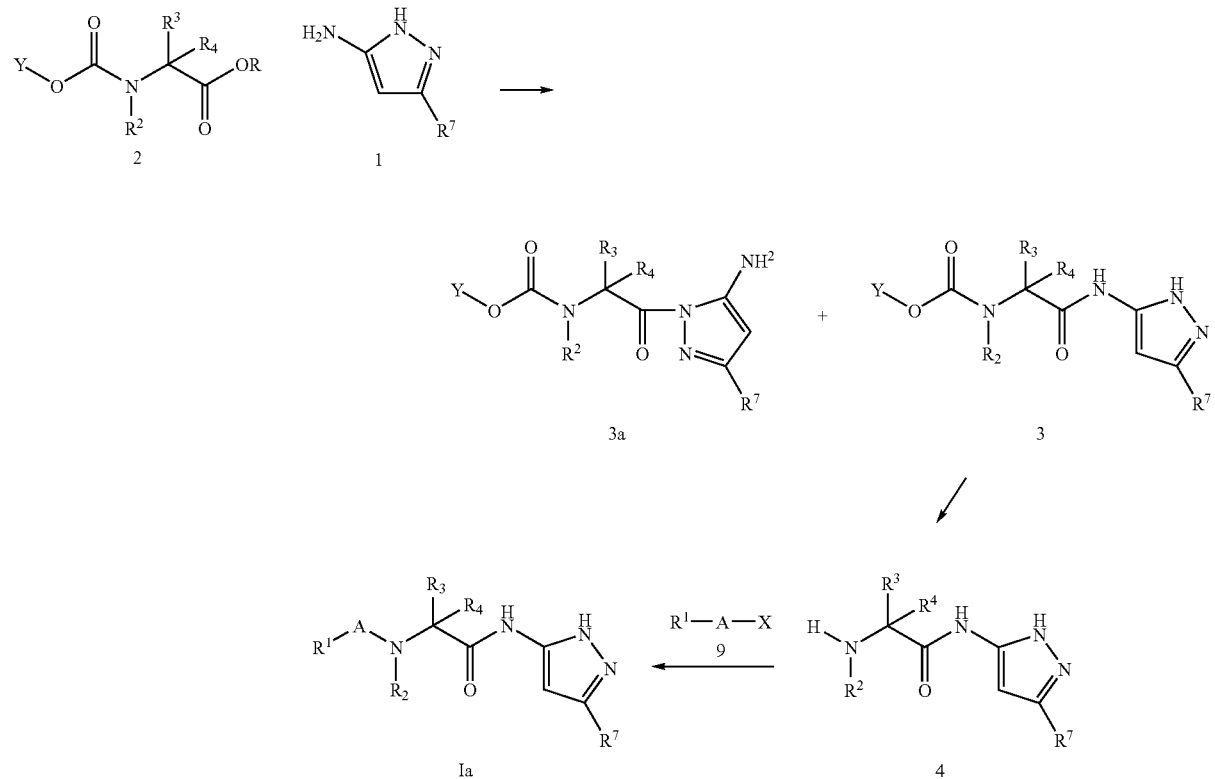

Scheme I

Scheme I refers to the preparation of compounds of the Formula I, Ia. An aminopyrazole 1 (5-substituted -2H-pyrazol-3-ylamine) or its corresponding tautomer (5-substituted-2H-pyrazol-3-ylamine) is coupled with a nitrogen-protected aminoacid 2. The nitrogen protecting group Y may be selected from any of the nitrogen protecting groups well known in the art, for example those described in literature such as Theodora W. Greene and Peter G. M. Wuts "Protective Groups in Organic Synthesis" Third Edition (1999). Examples of a protected nitrogen group for the reactant 2 include where —C(=O)OY in 2 is butoxycarbonyl ("BOC", Y=tert-butyl) or benzyloxycarbonyl ("CBZ", Y=benzyl), which are prepared with either di-tert-butyl dicarbonate (Aldrich Chemical Company, Milwaukee Wis.), or benzyl chloroformate (Aldrich) in the presence of either an inorganic or organic base (erg., sodium carbonate or triethylamine) at about 0 to about 30° C. in an organic solvent (e.g., methylene chloride) or in a mixture of water and an organic solvent (e.g., ethyl acetate) (Scheme II) (see, Muller, *Methoden Der Organischen Chemie.* "Vierte Auglage—Synthesis von Peptiden I"—Houben Weyl—Georg-Thieme Verlag Stuttgart, 1974, Band XW/1).

Scheme II

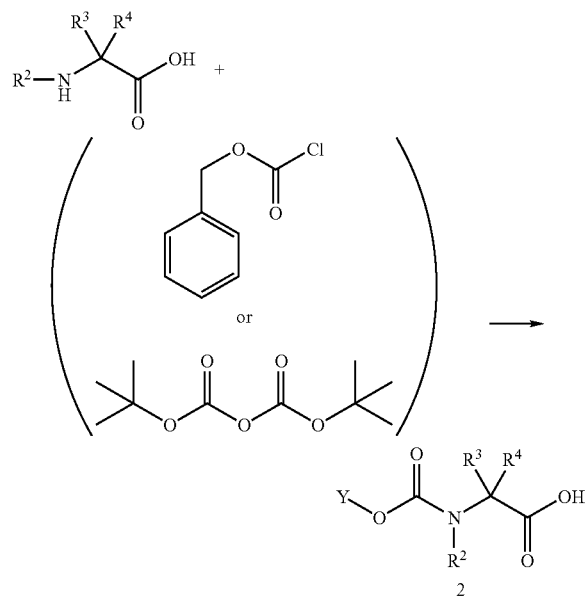

Intermediate 1 may be prepared according to procedure shown in Scheme III, using either a chlorovinylnitrile (Hartman, 1984, *Synthesis*, pp. 276-277) or a ketonitrile (Elnagdi, *Tetrahedron*, 1974, 31, 63).

Scheme III

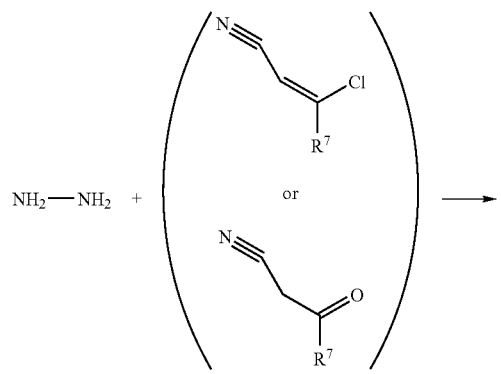

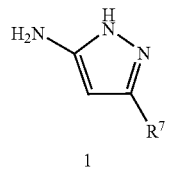

Numerous reagents, well-known in the art, can be used to couple 1 and 2 (wherein R is H) to form 3a or a mixture of 3a and 3 using standard peptide coupling methods known in art of organic chemistry (Scheme I). Activation of the carboxylic acid with HATU (O-(7-azabenzotriazole-1 yl)-1,1,3,3,-tetramethyluronium hexafluorophosphate) or PyBOP (benzotriazole-1-yl)-oxy-tris-pyrrolidino-phosphonium hexafluorophosphate) or TBTU in DMF with a base, like HBTU/trialkylamine, or HBOt/EDC/trialkylamine in an appropriate solvent such as methylene chloride, THF, DMF or a mixture of two solvents, and mixture of reagents mixed to form a clear solution. Many of these peptide coupling agents or resins for solid phase synthesis such as Fmoc (Fluorenylmethylcarbonyl)-protected hydroxylamine bound to polystylene beads is common and well known in literature. Deprotection of the Fmoc group can be accomplished under standard conditions using 20% piperidine in DMF. References: O-benzotriazol-1-yl-N,N,N',N'-tetramethyluronium hexafluorophosphate ("HBTU", Aldrich Chemical Company) and O-(7-azabenzotriazol-1-yl)-N,N,N',N'-tetramethyluronium hexafluorophosphate ("HATU", Aldrich) (See, Fieser, *Reagents for Organic Synthesis*, 1986, Wiley Interscience, New York, Vol. 12, p. 44; Hruby, *Biorganic Chemistry*: Peptides and Proteins, 1998, Oxford University press, New York, pp. 27-64; Muller, *Methoden Der Organischen Chemie*, Vierte Auflage—Synthese von Peptiden II—Houben Weyl, George-Thieme Verlag Stuttgart, 1974, Band XVI2). When optically active reagents are employed, reaction conditions, such as temperature, time and the selection of the base, must be carefully controlled to avoid racemization. The protected amino group or carboxylic acid group can be prepared by methods well known in the literature for amino acid protecting groups as described in Organic chemistry Journal, textbook such as "Protective Groups in Organic Syntehsis" by T. W. Greene and Wuts as described above. Compound 3a can be heated at an appropriate temperature from about 80 to about 180° C., preferably at about 150 to about 170° C. to provide compound 3.

Intermediate 3 of Scheme I, is deprotected to afford aminoamide 4 (or its corresponding 1H-pyrazol tautomer) either through treatment with strong acid in the case of butoxycarbonyl or through hydrogenolysis in the case of carbobenzyloxycarbonyl. Specifically, BOC-3, on treatment with hydrochloric acid or trifluoroacetic acid in an organic solvent (e.g., dioxane, THF, or methylene chloride), at about 30° C. for about 1 to about 19 hours affords the corresponding salts of 4. Alternatively, CBZ-3 may be deprotected through catalytic hydrogenolysis in the presence of hydrogen (from about 1 to about 10 atmospheres), a heavy metal catalyst (e.g., palladium on carbon or palladium hydroxide on carbon, 1 to 10 percent catalyst loading, present at about 0.01 to about 0.50 times the of substrate), and a solvent (e.g., methanol, ethanol or ethyl acetate) at from about 20 to about 50° C. from about 1 to about 19 hours.

Alternatively, intermediate 3 can be prepared by reacting 1 and 2 (wherein R is alkyl, such as methyl or ethyl) in the presence of trialkylaluminum (such as AlMe$_3$) in an appropriate solvent, such as THF/toluene or dichloroethaneltoluene or toluene, at a suitable temperature, for example at a temperature of from about room temperature to about reflux, in an atmosphere or pressure reactor or sealed system.

The compound Ia in Scheme I (or its corresponding 1H-pyrazol tautomer) is prepared from the reaction of 4 with 9 where X is a leaving group (e.g., halide or triflate). The reaction is carried out at about 0 to about 30° C. in an organic solvent (e.g., methylene chloride, ethyl acetate, or DMF) in the presence of an organic base (e.g., triethylamine, diisopropylethylamine, or N-methylmorpholine) from about 1 minute to about 24 hours. Alternatively, the compound Ia in Scheme I is prepared from the reaction of 4 with 9 where X is —OH using a standard amide coupling agent (such as HBOt/EDC/triethylamine in methylene chloride or DMF) similar to that described above for the conversion of 1 and 2 to 3a and/or 3.

Alternatively, the compound Ib can be prepared according to the procedure of Scheme IV, employing the general conditions described for Scheme I. In Scheme IV, R can be alkyl or benzyl. The coupling of 9 and 11 in Scheme IV can be performed between about 0 and about 30° C. in an organic solvent (e.g., methylene chloride, ethyl acetate, or DMF) in the presence of a base (e.g., triethylamine or diisopropylethylamine). When R is alkyl, either acidic or basic hydrolysis may be used to convert 12 to 13. If R is benzyl, catalytic hydrogenolysis may also be used to prepare 13.

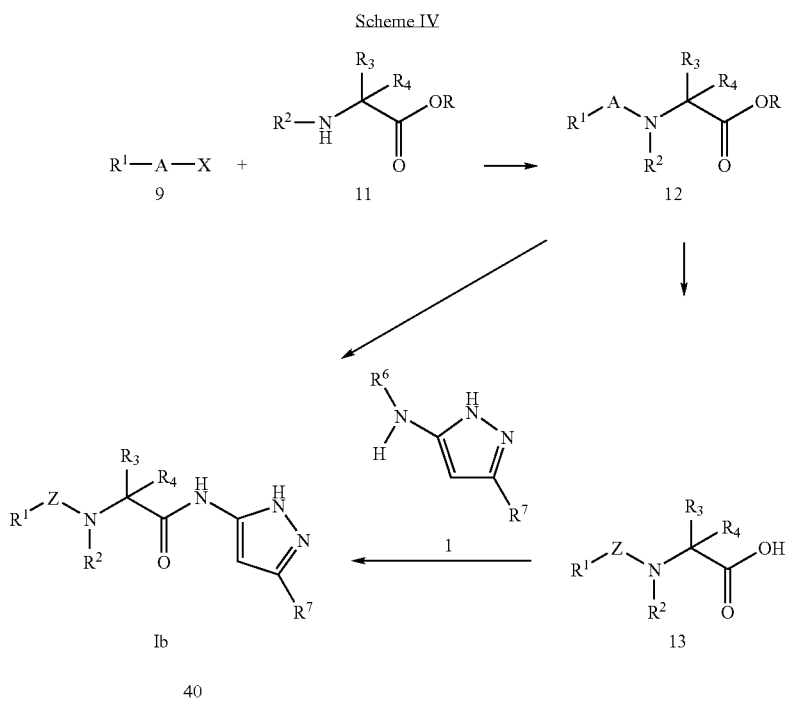

The above amide bond formation can be prepared from coupling of the ester (12 in Scheme IV) with 1 in the presence of trialkylaluminum (such as AlMe$_3$) in an appropriate solvent, eg., THF, toluene or a mixture of THF/toluene in an open or sealed tube at a temperature of between about 80 and about 150° C. until complete conversion to the desired product (Ib in Scheme IV).

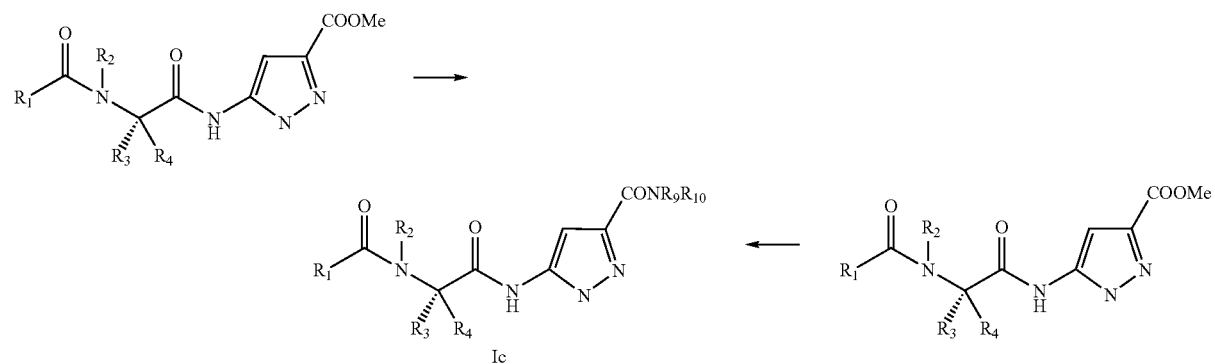

Scheme VI

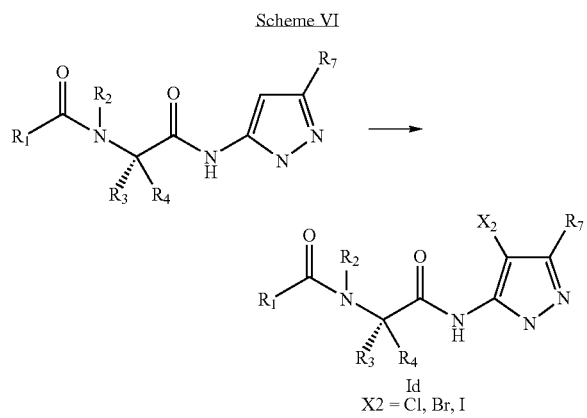

The ester group of $R^7$ can be converted to the corresponding amide using a similar method for amide bond formation, preferably using trimethylaluminum in an appropriate solvent or mixture of solvents, such as THF/toluene as shown in Scheme V.

The halo group $X^2$ can be generated according to Scheme VI by reacting the starting material wherein $R^5$ is H with NBS, NCS, $I_2$ in an appropriate solvents such as methylene chloride, or chloroform. The halo group can be replaced with another group using the methods known in art, such as halogen-metal exchange, followed by quenching with an electrophile, or using typical Suzuki coupling conditions employing a catalyst such as palladium complex like tetrakis(triphenylphosphine)-palladium with sodium carbonate as a base in a suitable solvent such as THF, DME, Ethanol and a boronic acid.

Regardless of the procedure used to prepare the compounds of formula I, purification may be accomplished by crystallization or using chromatography on silica gel either with an ethyl acetate/hexane elution gradient or a chloroform/methanol elution gradient.

Pharmaceutically acceptable salts of a compound of formula I can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously), rectally, or topically. In general, the daily dosage for treating a neurodegenerative disease or condition or a disease or condition associated with Aβ-peptide production will generally range from about 0.1 mg/kg to about 5 gm/kg body weight, preferably from about 0.1 mg/kg to about 100 mg/kg body weight. Variations based on the aforementioned dosage range may be made by a physician of ordinary skill taking into account known considerations such as the weight, age, and condition of the person being treated, the severity of the affliction, and the particular route of administration chosen.

A specific compound of formula I can be determined to inhibit Aβ-peptide production using biological assays known to those of ordinary skill in the art, for example the assays described below.

The activity of compounds of the invention in inhibiting gamma-secretase activity was determined in a solubilized membrane preparation generally according to the description provided in McLendon et al. *Cell-free assays for γ-secretase activity, The FASEB Journal* (Vol. 14, December 2000, pp. 2383-2386). Using such assay, compounds of the invention were determined to have an $IC_{50}$ activity for inhibiting gamma-secretase activity of less than about 32 micromolar. For example, Example 84, below, had an $IC_{50}$ of about 1 micromolar, and Example 138, below, had an $IC_{50}$ of about 5 micromolar.

The following Examples illustrate the present invention. It is to be understood, however, that the invention, as fully described herein and as recited in the claims, is not intended to be limited by the details of the following Examples.

EXAMPLES

General Procedures

Step A: Conversion of L-Norvaline To L-Norvaline-Methyl Ester.HCL 3.0 g (25.6 mmol, 1.0 Eq.) of L-Norvaline was dissolved in 50.0 mL of methanol and cooled to 0° C. This was saturated with HCl gas and gradually allowed to warm to room temperature. After 14 hours the solvent was removed and the solid was dried overnight in a dessicator with phosphorous pentachloride. 3.6 g (86%) of a white solid was obtained. (MS: 126.9/[P$^{-1}$]) (H$^1$NMR in CDCl$_3$: 0.95, 3H t, (J=382 Hz), 1.46, 2H m, (J=587 Hz), 2.01, 2H m, (J=806 Hz), 3.78, 3H s, (J=1512 Hz), 4.05, 1H m, (J=1622.459 Hz), 8.74, 2H brds, (J=3495 Hz))

Step B: Synthesis of 2-[2-(Difluoro-phenyl)-acetyl amino]-pentanoic acid methyl ester 1.0 g (7.8 mmol, 1.0 Eq.) of the title compound of Step A was combined in a flask at room temperature with 1.62 g (9.4 mmol, 1.2 Eq.) of (3,5-Difluoro-phenyl)-acetic acid, 4.1 g (9.4 mmol, 1.0 Eq.) of HBTU, 2.6 mL (18.7 mmol, 3.0 Eq.) of triethylamine, and 40 mL of dichloromethane. After stirring overnight at room temperature MS and TLC indicated reaction completion. Solution was extracted successively with 1N HCl, water, saturated sodium bicarbonate, water, and brine. This was dried over sodium sulfate and the solvent removed. The oil obtained was purified by flash chromatography using 4:1 Hexane:Ethyl Acetate as eluent. 800 mg (36%) of the desired product was obtained. (MS: 286.2 [P$^{+1}$]/284.1 [P$^{-1}$]) (R$_f$=0.70 on silica TLC with 1:1 Hexane/Ethyl Acetate) (H$^1$NMR in CDCl$_3$: 0.84, 3H t, (J=339 Hz), 1.27, 2H m, (J=510 Hz), 1.60, 1H m, (J=641.855), 1.773, 1H m, (J=708.639 Hz), 3.70, 3H s, (J=1478 Hz), 4.57, 1H m, (J=1828 Hz), 5.91, 1H brd d, (J=2362 Hz), 6.69, 1H m, (J=2677 Hz), 6.78, 2H m, (J=2712 Hz))

Step C: Conversion of 2-[2-(Difluoro-phenyl)-acetyl amino]-pentanoic acid methyl ester to 2-[2-(3.5-Difluoro-phenyl)-acetic acid 800 mg (2.8 mmol, 1.0 Eq.) of the title compound of Step B (2-[2-(difluoro-phenyl)-acetyl amino]-pentanoic acid methyl ester) was dissolved in a solution of 20 mL H$_2$O/20 mL tetrahydrofuran. 336 mg (14.0 mmol, 5.0 Eq.) of lithium hydroxide was added and this was allowed to stir at room temperature over night. The pH was adjusted to 1.0 with 6.0 N HCl and the solvent was stripped to ½ the original volume. 700 mg (92%) of the desired product precipitated out of solution. (MS: 272.2 [P$^{+1}$]/270.1 [P$^{-1}$]) (R$_f$ 0.30 (silica TLC in 9:1 Chloroform/Methanol) (H1NMR in CD$_3$OD: 0.88, 3H m, (J=354 Hz), 1.41, 2H m, (J=564 Hz), 1.65, 1H m, (J=622 Hz), 1.80, 1H m, (J=721 Hz), 3.55, 2H (J=1420 Hz), 4.32, 1H m, (J=1728 Hz), 6.80, 1H m, (J=2721 Hz), 6.90, 2H m, (J=2761 Hz).

Step D: Synthesis of N-[1-(5-Amino-3-phenyl-pyrazole-1-carbonyl)-butyl]-2-(3.5-diflouro-phenyl)-acetamide 220mg (1.38 mmol, 1.25 Eq.) of 5-amino-3-phenyl pyrazole was combined in a flask at room temperature with 595 mg (1.38 mmol, 1.25 Eq.) of HBTU, 0.4 mL (3.3 mmol, 3.0 Eq.) of N-methyl piperidine and 8 mL of dichloromethane. After 15 minutes 300 mg (1.1 mmol, 1.0 Eq.) of the product of Step C (2-[2-(3,5-difluoro-phenyl)-acetic acid) was added. MS and TLC indicated reaction completion after 2.5 hours. Solution was extracted successively with saturated sodium bicarbonate, water, and brine, was dried over sodium sulfate, and the solvent removed. The yellow solid obtained was purified by flash using 3:1 HexanelEthyl Acetate yielding 260 mg (57%) of a white solid. (MS: 413.1 [P$^{+1}$]/411.1 (P$^{-1}$]) (R$_f$=0.69 (silica TLC in 1:1 Hexane/Ethyl Acetate)) (H$^1$NMR in CD3OD: 0.95, 3H m, (J=380 Hz), 1.48, 2H m, (J=595 Hz), 1.97, 2H m, (J=789 Hz), 3.60, 2H s, (J=1439 Hz), 5.45, 1H s, (J=2180 Hz), 5.74, 1H m, (J=2296 Hz), 6.90, 1H m, (J=2760 Hz), 6.92, 2H m, (J=2767 Hz), 7.33, 5H m, (J=2933 Hz), 7.75, 2H d, (J=3100 Hz))

Step E: Rearrangement of N-[1-(5-Amino-3-phenyl-pyrazole-1-carbonyl]-butyl]-2-(3.5-difluoro-phenyl)-acetamide to 2-[2-(3,5-Difluoro-phenyl)-acetylamine]-pentanoic acid (5-phenyl-2H-pyrazole-3-yl)-amide 260 mg of the title compound of Step D (N-[1-(5-amino-3-phenyl-pyrazole-1-carbonyl)-butyl]-2-(3,5-diflouro-phenyl)-acetamide) was heated neat to 150° C. After 2 hours LC/MS indicated reaction completion. The solid was tritrated with hexane to give 240 mg of final product. (R$_f$=0.45 (silica TLC in 1:1 Hexane/Ethyl Acetate) (H$^1$NMR in CD$_3$OD: 0.93, 3H t, (J=372 Hz), 1.42, 2H m, (J=480 Hz), 1.67, 1H m, (J=520 Hz), 1.72, 1H m, (J=532 Hz), 3.59, 2H s, (J=1435 Hz), 4.23, 1H m, (J=1678 Hz), 6.79, 3H m, (J=2714.266 Hz), 6.90, 2H m, (J=2759 Hz), 7.37, 2H m, (J=2949 Hz), 7.39, 1H m, (J=2957 Hz), 7.39, 2H d, (J=2957 Hz))

Procedure for 2-[2-(3,5-Difluoro-phenyl)-acetylamino]-penatnoic acid (5-phenyl-2H-pyrazole-3-yl)-amide Step A: Synthesis of [1-(5-Amino-3-phenyl-pyrazole-1-carbonyl)-butyl]-carbamic acid tert-butyl ester 492 mg (2.26 mmol, 1.2 Eq.) of boc-norvaline was combined in a flask with 300 mg (1.9 mmol, 1.0 Eq.) of 5-amino-3-phenyl pyrazole, 0.80 mL (5.7 mmol, 3.0 Eq.) of triethylamine, 820 mg (1.9 mmol, 1.0 Eq.) of HBTU and 10 mL of anhydrous dichloromethane. After one hour of room temperature stirring MS and TLC indicated reaction completion. Solution was extracted with saturated sodium bicarbonate followed by water and brine. This was dried over sodium sulfate and the solvent removed. The yellow oil obtained was purified by flash chromatography using 3:1 Hexane/Ethyl Acetate as the solvent. 471 mg (69%) of yellow oil was obtained. (MS: 359/[P$^{+1}$]) (R$_f$=0.89 on silica TLC with 1:1 Hexane/Ethyl Acetate) (H$^1$NMR in CD$_3$OD: 0.95, 3H t, (J=383 Hz), 1.22, 9H s, (J=488 Hz), 1.41, 2H m, (J=567 Hz), 1.97, 2H m, (J=790 Hz), 5.40, 1H m, 5.75, 1H s, (J=2299 Hz), 7.35, 3 H m, (J=2938 Hz), 7.79, 2H m, (J=3115 Hz).

Step B: Rearrangement/BOC Removal To Give 2-Amino-1-(5-amino-3-phenyl-pyrazole-1-yl)-pentan-1-one Di-HCl Salt 471 mg of the title compound of Step A ([1-(5-amino-3-phenyl-pyrazole-1-carbonyl)-butyl]-carbamic acid tert-butyl ester) was taken up in 4.5 mL of a 4.0 N HCl dioxane solution and allowed to stir at room temperature. After 1 hour MS indicated reaction completions. The solvent was removed and the residue obtained was titrated with ether to give 250 mg (73%) of a white solid. (MS: 259.2 [P$^{+1}$]) (H$^1$NMR in DMSO: 0.87, 2H m, (J=350 Hz), 1.02, 3H t, (J=409 Hz), 1.29, 1H m, (J=518 Hz), 1.72, 1H m, (J=691 Hz), 3.51, 1H m, (J=1406 Hz), 6.86, 1H s, (J=2742 Hz), 7.41, 3H m, (J=2962 Hz), 7.67, 1H d, (J=3068 Hz), 7.37, 1H d, (J=3095 Hz), 8.23, 2H d, (J=3291 Hz).

Step C: Synthesis of 2-[2-(3,5-Difluoro-phenyl)-acetylamino]-pentanoic acid (5-phenyl-2H-pyrazole-3-yl)-amide 160 mg (0.62 mmol, 1.0 Eq.) of the title compound of Step C (2-amino-1-(5-amino-3-phenyl-pyrazole-1-yl)-pentan-1-one Di-HCl) was combined in a flask with 128 mg (0.74 mmol, 1.2 Eq.) of 3,5-Difluoro-phenyl acetic acid, 0.31 mL (2.2 mmol, 3.0 Eq.) of triethylamine, 267 mg (0.62 mmol, 1.0 Eq.) of HBTU and 10 mL of anhydrous dichloromethane. After 2 hours of room temperature stirring MS and TLC indicated reaction completion. Desired product was confirmed by H$^1$NMR and LC/MS.

Procedure For 2-Phenylmethanesulfonylamino-N-(5-phenyl-2H-pyrazol-3-yl)-propionamide Step A: Coupling of BOC-Ala With Aminopyrazole To Afford [1-(5-Phenyl-2H-pyrazol-3-ylcarbamoyl)-ethyl]-carbamic acid tert-butyl ester To 348 mg (2.2 mmol) of 5-phenyl-2Hpyrazol-3-ylamine (or its corresponding tautomer 5-phenyl-1H-pyrazol-3-ylamine) and 378 mg (2mm91) of BOD-L-alanine (Aldrich) in 4 ml of methylene chloride was added at 0° C. dropwise with stirring 0.61 ml (4.4 mmol) of thriethylamine, followed by 0.33 ml (3.3 mmol) of diethylcyanophosphonate after 20 min. The reaction was allowed to warm to room temperature and stirred for 24 hr. After determination that the reaction had proceeded to completion by TLC and mass spectroscopy, the methylen chloride was evaporated and the residue dissolved in ethylacetat. The organic layer was washed successively with 1N Hcl, SATD NaHCO$_3$, and brine, followed by drying with sodium sulfate. Evaporation yielded 770 mg of 1-(5-Phenyl-2H-pyrazol-3-ylcarbamoyl)-ethyl]-carbamic acid tert-butyl ester (quantitative) ( MS: 331 P+1/329 P−1) (RF=0.6 ON SILICA TLC (9/1 Chloroform/Methanol).

Step B: Deblocking of 1-(5-Phenyl-2H-pyrazol-3-ylcarbamoyl)-ethyl]-carbamic acid tert-butyl ester to Amino-N-(5-phenyl-2H-pvrazol-3-yl)-propionamide Dihydrochloride To 100 mg (0.30 mmol) of the product of Step A [1-(5-phenyl-2H-pyrazol-3-ylcarbamoyl)-ethyl]-carbamic acid tert-butyl ester was added 1 ml of 4N HCl dioxane solution (Aldrich) at ambient temperature. The reaction was allowed to stir for 3 hours. After evaporation to dryness and trituration with ether, 73 mg of amino-N-(5-phenyl-2H-pyrazol-3-yl)-propionamide dihydrochloride was obtained as a white powder (80%) ( MS: 231[P+1]/229 [P−1])(RF=0.2 on silica TLC (9/1 Chloroform/ Methanol).

Step C: Coupling of Benzylsulfonylchloride with amino-N-(5-phenyl-2H-pyrazol-3-yl)-propionamide dihydrochloride to afford Phenylmethanesulfonylamino-N-(5-phenyl-2H-pyrazol-3-yl)-propionamide To 73 mg of the produce of Step B (amino-N-(5-phenyl-2H-pyrazol-3-yl)-propionamide dihydrochloride) (0.24 mmol), triethylamine (0.10 ml, 0.72 mmol) in 2 ml of methylene chloride at 0° C. with stirring was added 46 mg (0.24 mmol) of benzyl sulfonyl chloride. After 1 hour the reaction was allowed to warm to ambient and stirred for 19 hours. Mass spectroscopy had indicated that the reaction had proceeded to completion. Using the workup procedure of Step A by trituration with ether yeilded 32 mg of pure phenyl-methanesulfonylamino-N-(5-phenyl-2H-pyrazol-3-yl)-propionamide 7 (35%) (MS: 385[P+1}/383[P−1]) (RF=0.75 (silica gel TLC with CHCl$_3$/CH$_3$OH 18/1)).

The following Examples of compounds of Formula I of the invention were prepared according to Schemes I-VI in the "Detailed Description of the Invention":

TABLE 1

Unless otherwise indicated, ($R^4$ = H)

| Ex | $R^1$ | $R^3$ | $R^6$ | $R^7$ | M + 1 (Mass spectra) |
|---|---|---|---|---|---|
| 1. | (benzothiophen-4-ylmethyl) | Me | H | Ph | 405.2 |
| 2. | (thiophen-2-yl-CH$_2$—) | Me | H | Ph | 355.1 |
| 3. | 4-F-Ph-CH(OH)— | Me | H | Ph | 383.3 |
| 4. | 4-Cl-Ph-CH(OH)— | Me | H | Ph | 399.3 |
| 5. | 3-Me-Ph-CH$_2$— | Me | H | Ph | 363.3 |
| 6. | 2,5-di-F-Me-Ph-CH$_2$— | Me | H | Ph | 385.3 |
| 7. | 4-CF$_3$-Ph-CH(OH)— | Me | H | Ph | 433.3 |
| 8. | PhCH(F)— | Me | H | Ph | 367.3 |
| 9. | 4-CF$_3$-Ph-CH$_2$— | Me | H | Ph | 417.3 |
| 10. | 3-CF$_3$-6-F-Ph-CH$_2$— | Me | H | Ph | 435.3 |
| 11. | 3-CF$_3$-4-F-Ph-CH$_2$— | Me | H | Ph | 435.3 |
| 12. | 2-OCF$_3$-PhCH$_2$— | Me | H | Ph | 433.1 |
| 13. | 3-PhO-PhCH$_2$— | Me | H | Ph | 441.1 |
| 14. | 4-OCF$_3$-PhCH$_2$— | Me | H | Ph | 433.1 |
| 15. | 3,5-di-F-PhCH(OH)— | Me | H | Ph | 401.3 |
| 16. | 3,5-di-F-PhCH(OAc)— | Me | H | Ph | 443.0 |
| 17. | 3,5-di-F-Ph-(S)-CH(OH)— | Me | H | Ph | 401.0 |
| 18. | 3,5-di-F-Ph-(R)-CH(OH)— | Me | H | Ph | 401.0 |
| 19. | 3,5-di-F-Ph-(S)-CH(OH)— | Et | H | Ph | 415.0 |
| 20. | 3,5-di-F-Ph-(R)-CH(OH)— | Et | H | Ph | 415.0 |
| 21. | 3-pyridyl-CH$_2$— | Et | H | Ph | 364.1 |
| 22. | 2-pyridyl-CH$_2$— | Et | H | Ph | 364.1 |

TABLE 1-continued

Structure: R¹-C(=O)-NH-CH(R³)(R⁴)-C(=O)-NH-(pyrazole with R⁶ at 4-position, R⁷ at 3-position)

Unless otherwise indicated, (R⁴ = H)

| Ex | R¹ | R³ | R⁶ | R⁷ | M + 1 (Mass spectra) |
|---|---|---|---|---|---|
| 23. | 5-Br-pyridin-3-yl-CH₂— | Et | H | Ph | 443.9 |
| 24. | cyclopentyl-CH₂-CH₂— | Et | H | Ph | 369.2 |
| 25. | 2-phenylcyclopropyl-CH— | Et | H | Ph | 389.2 |
| 26. | MeO-C(=O)-CH₂-CH₂— | Et | H | Ph | 359.2 |
| 27. | t-Bu-CH₂— | Et | H | Ph | 343.3 |
| 28. | C₁₁H₂₁— | Et | H | Ph | 427.4 |
| 29. | PhCH₂— | Et | H | Ph | 363.3 |
| 30. | C₅H₁₁— | Et | H | Ph | 343.4 |
| 31. | C₆H₁₃— | Et | H | Ph | 357.4 |
| 32. | Cl—CH₂CH₂— | Et | H | Ph | 335.3 |
| 33. | PhCH₂CH₂— | Et | H | Ph | 377.3 |
| 34. | Me₂CHCH₂— | Et | H | Ph | 329.3 |
| 35. | C₉H₁₉— | Et | H | Ph | 399.4 |
| 36. | C₃H₇— | Et | H | Ph | 315.4 |
| 37. | Cl—(CH₂)₃—CH₂— | Et | H | Ph | 363.2 |
| 38. | 3-PhO-PhCH₂— | Et | H | Ph | 455.3 |
| 39. | N-Boc-piperidin-3-yl-CH₂— | Et | H | Ph | 470.4 |
| 40. | 3-CF₃-Ph-CH₂— | Et | H | Ph | 431.3 |
| 41. | 3-I-PhCH₂— | Et | H | Ph | 489.2 |
| 42. | 3-Cl-Ph-CH₂— | Et | H | Ph | 397.3 |
| 43. | 3-PhO-PhCH₂— | —CH₂CH₂SMe | H | Ph | 501.3 |
| 44. | Me₂CHCH₂— | —CH₂CH₂SMe | H | Ph | 405.1 |
| 45. | 3,5-di-F-Ph-CH(OH)— | CH₂CH₂SMe | H | Ph | 461.0 |
| 46. | CH₃— | CH₂CH₂SMe | H | Ph | 333.0 |
| 47. | 3,5-di-F-PhCH₂— | Et | H | COOEt | 395.0 |
| 48. | Me₂CHCH₂—CH(OH)— | Et | H | COOEt | 355.1 |
| 49. | 3,5-di-F-PhCH(OH)— | Et | H | COOEt | 411.0 |
| 50. | 3,5-di-F-Ph-CH₂— | Et | H | CH₂OH | 353.0 |
| 51. | 3,5-di-F-Ph-CH₂— | Et | H | CONHNH₂ | 381.3 |
| 52. | 3,5-di-F-Ph-CH₂— | Et | H | Ph | 466.3 |
| 53. | 3,5-di-F-Ph-CH₂— | Et | H | —CONH₂ | 366.1 |
| 54. | 3,5-di-F-Ph-CH₂— | Et | H | —CONHMe | 380.3 |
| 55. | 3,5-di-F-Ph-CH₂— | Et | H | —CONHCH(Et)₂ | 436.3 |
| 56. | 3,5-di-F-Ph-CH₂— | Et | H | —CON(Et)(n-Bu) | 450.3 |

TABLE 1-continued

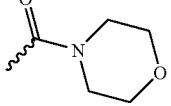

Unless otherwise indicated, (R⁴ = H)

| Ex | R¹ | R³ | R⁶ | R⁷ | M + 1 (Mass spectra) |
|---|---|---|---|---|---|
| 57. | 3,5-di-F-Ph-CH$_2$— | Et | H | —CONHCH-cyclopropyl | 420.3 |
| 58. | 3,5-di-F-Ph-CH$_2$— | Et | H | 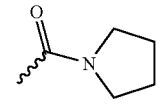 | 436.5 |
| 59. | 3,5-di-F-Ph-CH$_2$— | Et | H | 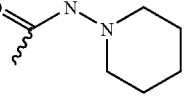 | 420.3 |
| 60. | 3,5-di-F-Ph-CH$_2$— | Et | H | 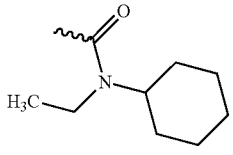 | 449.5 |
| 61. | 3,5-di-F-Ph-CH$_2$— | Et | H | —CONHCH(Me)(Et) | 422.4 |
| 62. | 3,5-di-F-Ph-CH$_2$— | Et | H | —CON(Et)(CH$_2$CH$_2$OH) | 438.4 |
| 63. | 3,5-di-F-Ph-CH$_2$— | Et | H |  | 476.4 |
| 64. | 3,5-di-F-Ph-CH$_2$— | Et | H | —CON(allyl)$_2$ | 446.0 |
| 65. | 3,5-di-F-Ph-CH$_2$— | Me | H | Ph | 385.1 |
| 66. | 3,5-di-F-Ph-CH$_2$— | CH(Me)(Et) | H | Ph | 427.2 |
| 67. | 3,5-di-F-Ph-CH$_2$— | CH(Me)(Et) | H | Cyclobutyl | 405.2 |
| 68. | PhCH$_2$— | Me | H | Ph | 349.1 |
| 69. | 3-F-PhCH$_2$— | Me | H | Ph | 367.1 |
| 70. | 3,5-di-F-Ph-CH$_2$— | Me | H | Ph | 485.0 |
| 71. | 3,5-di-F-Ph-CH$_2$— | Me | H | —COO(n-Bu) | 409.1 |
| 72. | 3,5-di-F-Ph-CH$_2$— | Me | H | -3-indolyl | 424.1 |
| 73. | 3,5-di-F-Ph-CH$_2$— | Me | H | -4-t-Bu-Ph | 441.1 |
| 74. | 3,5-di-F-Ph-CH$_2$— | Me | H | -4-Et-Ph | 413.0 |
| 75. | 3,5-di-F-Ph-CH$_2$— | Me | H | —COOEt | 381.0 |
| 76. | 3,5-di-F-Ph-CH$_2$— | Me | Br | Ph | 462.9, 464.9 |
| 77. | 3,5-di-F-Ph-CH$_2$— | CR³R⁴: cyclopentyl | H | Ph | 425.0 |
| 78. | 3,5-di-F-Ph-CH2— | Me | Cl | Ph | 419.0 |
| 79. | 3,5-di-F-Ph-CH$_2$— | —CH$_2$CH═CH$_2$— | H | Ph | 411.0 |
| 80. | 3,5-di-F-Ph-CH$_2$— | Me | H | —CONH—(S)—CH(Ph)(COO-t-Bu) | 542.0 |
| 81. | 3,5-di-F-Ph-CH$_2$— | Me | H | —CONHCH$_2$Ph | 442.0 |
| 82. | 3,5-di-F-Ph-CH$_2$— | —CH$_2$CH═CH$_2$ | Br | ∿Ph | 488.9, 490.0 |
| 83. | 3,5-di-F-Ph-CH$_2$— | Me | H | —COOMe | 367.0 |
| 84. | 3,5-di-F-Ph-CH$_2$— | Ph | H | ∿Ph | 447.2 |
| 85. | 3,5-di-F-Ph-CH$_2$— | —CH$_2$CH═CH$_2$ | H | ∿Ph | 427.1 |

TABLE 1-continued

Unless otherwise indicated, (R⁴ = H)

| Ex | R¹ | R³ | R⁶ | R⁷ | M + 1 (Mass spectra) |
|---|---|---|---|---|---|
| 86. | 3,5-di-F-Ph-CH(OH)— | —CH₂COOMe | H | ⁓Ph | 459.1 |
| 87. | 3,5-di-F-Ph-CH₂— | cyclohexyl | H | ⁓Ph | 453.2 |
| 88. | 3,5-di-F-Ph-CH(OH)— | cyclohexyl | H | ⁓Ph | 469.2 |
| 89. | 3,5-di-F-Ph-CH(OH)— | —CH₂COOCH₂Ph | H | ⁓Ph | 519.2 |
| 90. | 3,5-di-F-Ph-CH(OH)— | CH₂CH=CH₂ | H | 2-thiophenyl⁓ | 397.1 |
| 91. | 3,5-di-F-Ph-CH₂— | n-Pr | | | 427.2 |
| 92. | norbornyl-CH₂— | n-Pr | H | ⁓Ph | 395.3 |
| 93. | cyclohexyl-CH₂— | n-Pr | H | Ph | 383.3 |
| 94. | PhCH(CH₂OH)— | n-Pr | H | Ph | 407.3 |
| 95. | adamantyl-CH₂— | n-Pr | H | Ph | 435.3 |
| 96. | Me₂CHCH₂CH₂— | n-Pr | H | Ph | 357.3 |
| 97. | (CH₃)₂CHCH(CH₃)-CH₂— | n-Pr | H | Ph | 357.3 |
| 98. | cyclopentyl-CH₂— | n-Pr | H | Ph | |
| 99. | cyclopropyl-CH₂— | n-Pr | H | Ph | 341.2 |
| 100. | indanyl-CH₂— | n-Pr | H | Ph | 417.3 |
| 101. | PhCH(Me)CH₂— | n-Pr | H | Ph | 405.3 |
| 102. | MeC(O)CH₂CH₂CH₂— | n-Pr | H | Ph | 371.3 |
| 103. | 3-Cl-Ph-CH₂— | n-Pr | H | Ph | 411.2 |
| 104. | 3-Br-PhCH₂— | n-Pr | H | Ph | 455.2, 457.2 |
| 105. | 3,5-di-F-Ph-CH₂— | Me | H | 2-furanyl | |

TABLE 1-continued

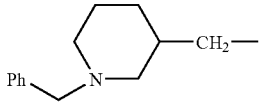

Unless otherwise indicated, (R⁴ = H)

| Ex | R¹ | R³ | R⁶ | R⁷ | M + 1 (Mass spectra) |
|---|---|---|---|---|---|
| 106. | 3,5-di-F-Ph-CH$_2$— | Me | H | t-Bu | |
| 107. | 3,5-di-F-Ph-CH$_2$— | Me | H | cyclopropyl | |
| 108. | 3,5-di-F-Ph-CH$_2$— | n-Pr | H | 2-furanyl | 403.4 |
| 109. | 3,5-di-F-Ph-CH$_2$— | n-Pr | H | 2-furanyl | 419.1 |
| 110. | 3,5-di-F-Ph-CH$_2$— | n-Pr | H | t-Bu | 393.2 |
| 111. | 3,5-di-F-Ph-CH$_2$— | n-Pr | H | 4-Cl-Ph | 447.4 |
| 112. | 3,5-di-F-Ph-CH$_2$— | i-Pr | H | t-Bu | 393.3 |
| 113. | 3,5-di-F-Ph-CH$_2$— | CR³R⁴:C(CH$_2$)$_2$ | H | t-Bu | 378.2 |
| 114. | 3,5-di-F-Ph-CH$_2$— | CR³R⁴:C(CH$_2$)$_2$ | H | 2-furanyl | 387.2 |
| 115. | 3,5-di-F-Ph-CH$_2$— | Me | H | -1-Ph-4-Ph | |
| 116. | 3,5-di-F-Ph-CH$_2$— | Me | H | -1-Ph-4-(4-di-Me-Ph) | |
| 117. | 3,5-di-F-Ph-CH$_2$— | n-Pr | H | Ph | |
| 118. | 3,5-di-F-Ph-CH$_2$— | Et | H | —C(═O)N(Me)(CH$_2$Ph) | 470.4 |
| 119. | 3,5-di-F-Ph-CH$_2$— | Et | H | —C(═O)N(Me)(CH$_2$Ph) | 470.4 |
| 120. | Me$_2$C═CHCH$_2$CH$_2$CHMeCH$_2$— | n-Pr | H | -Ph | 411.4 |
| 121. | 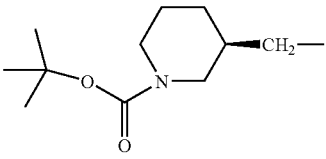 | Et | H | -Ph | 460.4 |
| 122. | 3,5-di-F-Ph-CH$_2$— | Et | H | —C(═O)N(n-Bu)$_2$ | 478.6 |
| 123. | 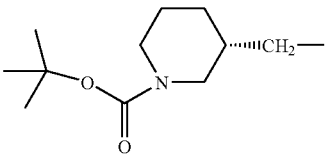 | Et | H | -Ph | 470.4 |
| 124. | 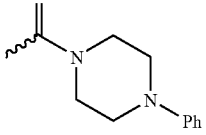 | Et | H | -Ph | 470.4 |
| 125. | 3,5-di-F-Ph-CH$_2$— | Et | H | —C(═O)NMeEt | 408.3 |
| 126. | 3-Cl-Ph-CH$_2$— | n-Pr | H | -Ph-4-Cl | 445.3 and 448.3 |
| 127. | 3,5-di-F-Ph-CH$_2$— | Et | H | 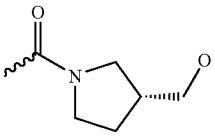 | 511.6 |
| 128. | 3,5-di-F-Ph-CH$_2$— | Et | H |  | 450.4 |
| 129. | Cyclohexyl-(R)-CH(OH) | n-Pr | H | Ph | 399.3 |
| 130. | Cyclohexyl-(S)-CH(OH) | n-Pr | H | Ph | 399.4 |

TABLE 1-continued

Unless otherwise indicated, (R⁴ = H)

| Ex | R¹ | R³ | R⁶ | R⁷ | M + 1 (Mass spectra) |
|---|---|---|---|---|---|
| 131. | 3,5-di-F-Ph-CH$_2$— | Et | H | (2,6-dimethylmorpholin-4-yl)carbonyl | 464.4 |
| 132. | 3,5-di-F-Ph-CH$_2$— | Et | H | —C(=O)N(n-Pr)(CH$_2$CH$_2$OH) | 452.4 |
| 133. | 3,5-di-F-Ph-CH$_2$— | Et | H | (3-ethoxycarbonylpiperidin-1-yl)carbonyl | 506.4 |
| 134. | 3,5-di-F-Ph-CH$_2$— | Et | H | C(=O)NMe(CH$_2$CHOMe$_2$) | 468.6 |
| 135. | 3,5-di-F-Ph-CH$_2$— | Et | H | —C(=O)N(CH$_2$CHMe$_2$)$_2$ | 422.4 |
| 136. | 3,5-di-F-Ph-CH$_2$— | Et | H | —C(=O)NEt$_2$ | 478.5 |
| 137. | (R)-citronellyl | n-Pr | H | Ph | 411.4 |
| 138. | (S)-citronellyl | n-Pr | H | Ph | 411.4 |
| 139. | 3,5-di-F-Ph-CH$_2$— | Et | H | —C(=O)N(CH$_2$Ph)$_2$ | 546.4 |
| 140. | 3,5-di-F-Ph-CH$_2$— | Et | H | (2-ethylpiperidin-1-yl)carbonyl | 462.4 |
| 141. | 3,5-di-F-Ph-CH$_2$— | Et | H | —C(=O)N(CH$_2$Ph)Et | 484.6 |
| 142. | 3,5-di-F-Ph-CH$_2$— | Et | H | —C(=O)NMe(n-Bu) | 436.6 |
| 143. | 3,5-di-F-Ph-CH$_2$— | Et | H | —C(=O)N(n-C$_6$H$_13$)$_2$ | 534.5 |
| 144. | 2,3-di-F-Ph-CH(OH)— | n-Pr | H | -Ph | 429.1 |
| 145. | (1-phenylsulfonylpiperidin-3-yl)CH$_2$— | Et | H | -Ph | 509.6 |
| 146. | (1-acetylpiperidin-3-yl)CH$_2$— | Et | H | -Ph | 412.4 |

TABLE 1-continued

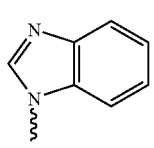

Unless otherwise indicated, (R⁴ = H)

| Ex | R¹ | R³ | R⁶ | R⁷ | M + 1 (Mass spectra) |
|---|---|---|---|---|---|
| 147. | 3,5-di-F-Ph-CH₂— | Et | H | —C(=O)N(n-C₃H₈)₂ | 450.6 |
| 148. | 3,5-di-F-Ph-CH₂— | Et | H | 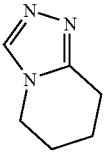 | 453.4 |
| 149. | 5-Br-3-pyridyl-CH₂— | n-Pr | H | -Ph-4-Cl | 492.3 |
| 150. | 3-CF₃-Ph-CH₂— | n-Pr | H | -Ph-4-Cl | 479.3 |
| 151. | 3-MeO-Ph-CH₂— | n-Pr | H | -Ph-4-Cl | 441.4 |
| 152. | 5-Ph-3-Py-CH₂— | Et | H | -Ph-4-Cl | 440.4 |
| 153. | 3,5-di-F-Ph-CH₂— | Et | H | —C(=O)N(n-C₅H₁₁)₂ | 506.5 |
| 154. | n-Bu-CH(OH)— | n-Pr | H | -Ph | 373.2 |
| 155. | 2-Cl-Ph-CH(OH)— | n-Pr | H | -Ph | 427.1 |
| 156. | 3,5-di-F-Ph-CH₂— | n-Pr | H | -H | 337.3 |
| 157. | 3,5-di-F-Ph-CH₂— | N-Pr | H | (attached to 2-triazolo-) | 444.6 |
| 158. | 3,5-di-F-Ph-CH₂— | t-Bu | H | -Ph | 427.3 |
| 159. | i-Pr-(S)-CH(OH)— | n-Pr | H | -Ph | 359.4 |
| 160. | 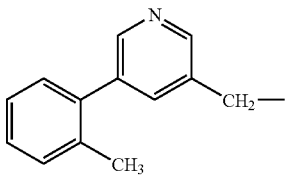 | N_pr | H | -Ph-4-Cl | 502.6 and 504.6 |
| 161. | i-Pr-(S)-CH(OH)— | Et | H | -Ph | 345.4 |
| 162. | 3,5-di-F-Ph-CH₂— | n-Pr | H | Me | 351.4 |
| 163. | 3,5-di-F-Ph-CH₂— | n-Bu | H | H | 427.3 |

TABLE 2

| Ex | R¹ | R³ | R⁷ | MS (M + 1) |
|---|---|---|---|---|
| 164. | PhCH₂— | Me | Ph | 385 |
| 165. | 4-F-PhCH₂— | Me | Ph | 403 |
| 166. | 2-NO₂-Ph-CH₂— | Me | Ph | 430 |
| 167. | PhCH₂— | n-Pr | t-Bu | 393 |
| 168. | 4-F-PhCH₂— | n-Pr | t-Bu | 411 |
| 169. | PhCH₂— | Me | t-Bu | |

TABLE 2-continued
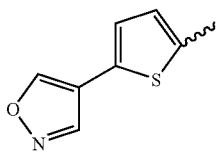
| Ex | R¹ | R³ | R⁷ | MS (M + 1) |
|---|---|---|---|---|
| 170. | 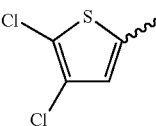 | n-Pr | Ph | 488 |
| 171. | 2-NO₂-PhCH₂— | n-Pr | Ph | 474 |
| 172. | 3-Me-PhCH₂— | n-Pr | Ph | 443 |
| 173. | 4-F-PhCH₂— | n-Pr | Ph | 447 |
| 174. | Ph- | n-Pr | Ph | 415 |
| 175. | 3,5-di-F-PhCH₂— | n-Pr | Ph | 465 |
| 176. | 4-PhO-Ph— | n-Pr | Ph | 507 |
| 177. | 3,5-di-Cl-Ph-CH₂— | n-Pr | Ph | 498 |
| 178. | 4-Me-Ph-CH₂— | n-Pr | t-Bu | 407 |
| 179. | Ph-CH₂— | n-Pr | Ph | 413 |
| 180. | C₁₀H₂₁— | n-Pr | Ph | 463 |
| 181. | 4-Ph-Ph— | n-Pr | Ph | 475 |
| 182. | 4-Cl-Ph-CH₂— | n-Pr | Ph | 447 |
| 183. | Ph | —CH₂CH₂SMe | Ph | 431.0 |
| 184. | 4-F-PhCH₂— | n-Pr | Ph | 433.2 |
| 185. | 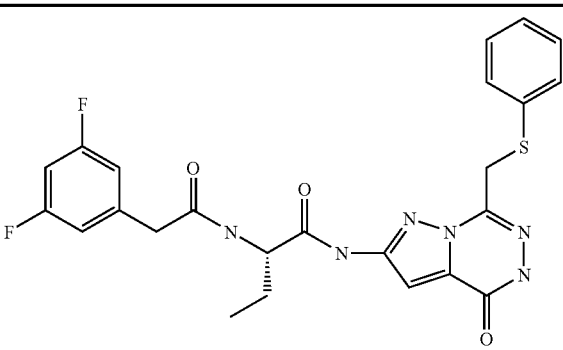 | —CH₂CH₂SMe | Ph | 506.8 |
| 186. | 4-Cl-PhCH₂— | n-Pr | t-Bu | 429.6 |
TABLE 3
| Pfizer number | Structure | MS (M + 1) |
|---|---|---|
| 187. | 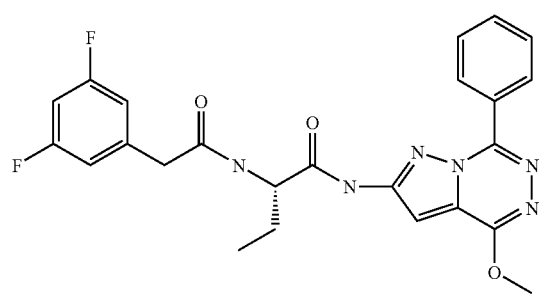 | 427.2 |
| 188. | 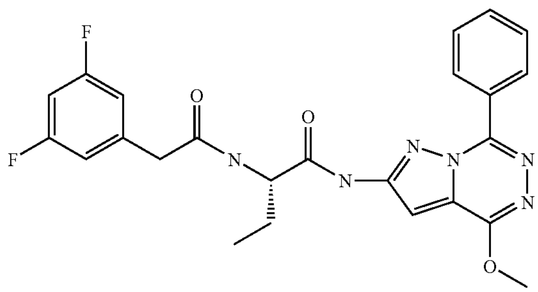 | 513.2 |

TABLE 3-continued

| Pfizer number | Structure | MS (M + 1) |
|---|---|---|
| 189. | 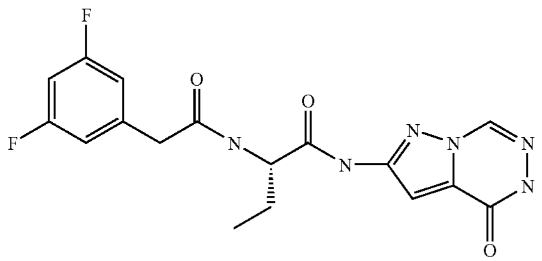 | 481.1 |
| 190. | 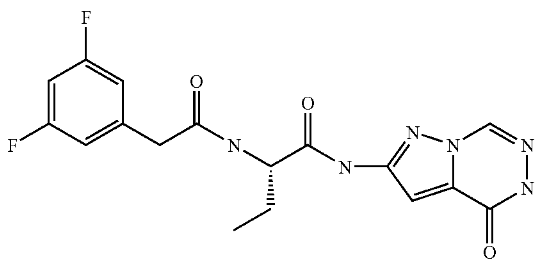 | 391.3 |

The invention claimed is:

1. A compound of Formula:

or a pharmaceutically acceptable salt thereof, wherein:

A is —C(=O)Z—;
Z is selected from —CH$_2$—, —CH(OH)—, —CH(NH$_2$)—, —CH(CH$_2$(CH))—, —CH(CH(C$_1$-C$_4$ alkyl)(OH))—, and —CH(C(C$_1$-C$_4$ alkyl)(C$_1$-C$_4$ alkyl)(OH))—;
R$^1$ is selected from C$_3$-C$_8$ cycloalkyl, (C$_4$-C$_8$)cycloalkenyl, (C$_5$-C$_{11}$)bi- or tricycloalkyl, (C$_7$-C$_{11}$)bi- or tricycloalkenyl, and (C$_6$-C$_{14}$)aryl wherein each said cycloalkyl, cycloalkenyl, bi- or tricycloalkyl, bi- or tricycloalkenyl, and aryl is optionally substituted with from one to three substituents R$^{1b}$;
R$^{1b}$ is in each instance independently selected from —Cl, —F, —Br, —I, —CN, and —NO$_2$;
R$^2$ is —H or —C$_1$-C$_4$ alkyl;
R$^3$ is selected from C$_1$-C$_6$ alkyl, —C$_2$-C$_6$ alkenyl, and —C$_2$-C$_6$ alkynyl;
R$^4$ is —H or C$_1$-C$_4$alkyl;
R$^6$ is selected from —H, —C$_1$-C$_{20}$ alkyl, —Cl, —F, —Br, —I, —CN, and —CF$_3$;
R$^7$ is —(C$_{zero}$-C$_4$ alkylene)-((C$_6$-C$_{14}$)aryl) or —(C$_{zero}$-C$_4$ alkylene)-((5-15 membered) heteroaryl); wherein each R$^7$ is optionally substituted with from one to three substituents independently selected from —OH, —C$_1$-C$_6$ alkyl, —C$_1$-C$_6$ alkoxy, —Cl, —F, —Br, —I, —CN, and —NO$_2$; and
R$^8$ is —H or —C$_1$-C$_4$ alkyl.

2. A compound of claim 1, or a pharmaceutically acceptable salt thereof, wherein:

Z is —CH$_2$— or —CH(OH)—;
R$^1$ is (C$_6$-C$_{14}$)aryl; wherein said aryl is optionally substituted with from one to three substituents R$^{1b}$;
R$^2$ is —H or —C$_1$-C$_4$ alkyl;
R$^3$ is —C$_1$-C$_6$ alkyl;
R$^4$ is —H or —C$_1$-C$_4$ alkyl;
R$^6$ is selected from —H, —C$_1$-C$_{20}$ alkyl, —Cl, —F, —Br, —I, —CN, and —CF$_3$;
R$^7$ is —(C$_{zero}$-C$_4$ alkylene)-((C$_6$-C$_{14}$)aryl) or —(C$_{zero}$-C$_4$ alkylene)-((5-15 membered) heteroaryl); wherein each R$^7$ is optionally substituted with from one to three substituents independently selected from —OH, —C$_1$-C$_6$ alkyl, —C$_1$-C$_6$ alkoxy, —Cl, —F, —Br, —I, —CN, and —NO$_2$; and
R$^8$ is —H or —C$_1$-C$_4$ alkyl.

3. A compound of claim 1, or a pharmaceutically acceptable salt thereof, wherein:

Z is —CH$_2$— or —CH(OH)—;
R$^1$ is (C$_6$-C$_{14}$)aryl; wherein said aryl is optionally substituted with from one to three substituents R$^{1b}$;
R$^2$ is —H;
R$^3$ is —C$_1$-C$_6$ alkyl;
R$^4$ is —H or —C$_1$-C$_4$ alkyl;
R$^6$ is selected from —H, —C$_1$-C$_{20}$ alkyl, —Cl, —F, —Br, —I, —CN, and —CF$_3$;
R$^7$ is —(C$_{zero}$-C$_4$ alkylene)-((C$_6$-C$_{14}$aryl) or —(C$_{zero}$-C$_4$ alkylene)-((5-15 membered) heteroaryl); wherein each R$^7$ is optionally substituted with from one to three substituents independently selected from —OH, —C$_1$-C$_6$ alkyl, —C$_1$-C$_6$ alkoxy, —Cl, —F, —Br, —I, —CN, and —NO$_2$; and
R$^8$ is —H or —C$_1$-C$_4$ alkyl.

4. A compound of claim 1, or a pharmaceutically acceptable salt thereof, wherein:

Z is —CH$_2$— or —CH(OH)—;
R$^1$ is (C$_6$-C$_{14}$)aryl; wherein said aryl is optionally substituted with from one to three substituents R$^{1b}$;
R$^2$ is —H;

$R^3$ is —$C_1$-$C_6$ alkyl;
$R^4$ is —H or —$C_1$-$C_4$ alkyl;
$R^6$ is selected from —H, —$C_1$-$C_{20}$ alkyl, —Cl, —F, —Br, —I, —CN, and —$CF_3$;
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, —F, —Br, —I, —CN, and —$NO_2$; and
$R^8$ is —H or —$C_1$-$C_4$ alkyl.

5. A compound of claim 1, or a pharmaceutically acceptable salt thereof, wherein:
Z is —$CH_2$— or —CH(OH)—;
$R^1$ is ($C_6$-$C_{14}$)aryl; wherein said aryl is optionally substituted with from one to three substituents $R^{1b}$;
$R^2$ is —H;
$R^3$ is —$C_1$-$C_6$ alkyl;
$R^4$ is —H;
$R^6$ is —H;
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, and —F; and
$R^8$ is —H or —$C_1$-$C_4$ alkyl.

6. A compound of claim 1, or a pharmaceutically acceptable salt thereof, wherein:
Z is —$CH_2$— or —CH(OH)—;
$R^1$ is ($C_6$-$C_{14}$)aryl, wherein said aryl is optionally substituted with from one to three substituents $R^{1b}$;
$R^{1b}$ is in each instance —F;
$R^2$ is —H;
$R^3$ is —$C_1$-$C_6$ alkyl;
$R^4$ is —H;
$R^6$ is —H;
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, and —F; and
$R^8$ is —H or —$C_1$-$C_4$ alkyl.

7. A compound of claim 1, or a pharmaceutically acceptable salt thereof, wherein:
Z is —$CH_2$— or —CH(OH)—;
$R^1$ is ($C_6$-$C_{14}$)aryl; wherein said aryl is optionally substituted with from one to three substituents $R^{1b}$;
$R^{1b}$ is in each instance —F;
$R^2$ is —H;
$R^3$ is —$C_1$-$C_6$ alkyl;
$R^4$ is —H;
$R^6$ is —H;
$R^7$ is (5-15 membered) heteroaryl, optionally substituted with from one to three substituents independently selected from —OH, —$C_1$-$C_6$ alkyl, —$C_1$-$C_6$ alkoxy, —Cl, and —F; and
$R^8$ is —H or —$C_1$-$C_4$ alkyl.

8. A compound of claim 1, or a pharmaceutically acceptable salt thereof, wherein:
Z is —$CH_2$— or —OH(OH)—;
$R^1$ is ($C_6$-$C_{14}$)aryl; wherein said aryl is optionally substituted with from one to three substituents $R^{1b}$;
$R^{1b}$ is in each instance —F;
$R^2$ is —H;
$R^3$ is —$C_1$-$C_6$ alkyl;
$R^4$ is —H;
$R^6$ is —H;

$R^7$ is ($C_6$-$C_{14}$)aryl, optionally substituted with from one to three substituents independently selected from —OH, —$C_1$-$C_6$ alkyl, —$C_1$-$C_6$ alkoxy, —Cl, and —F; and
$R^8$ is —H or —$C_1$-$C_4$ alkyl.

9. A compound of claim 1, or a pharmaceutically acceptable salt thereof, wherein:
Z is —$CH_2$— or —CH(OH)—;
$R^1$ is ($C_6$-$C_{14}$)aryl; wherein said aryl is optionally substituted with from one to three substituents $R^{1b}$;
$R^{1b}$ is in each instance —F;
$R^2$ is —H;
$R^3$ is n-propyl;
$R^4$ is —H;
$R^6$ is —H;
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, and —F; and
$R^8$ is —H or —$C_1$-$C_4$ alkyl.

10. A compound of formula:

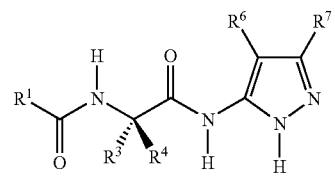

wherein:
$R^1$ is —($CH_2$)-(($C_6$-$C_{14}$)aryl) or —CH(OH)—(($C_6$-C14aryl), wherein said aryl is optionally substituted with from one to three substituents $R^{1b}$;
$R^{1b}$ is in each instance independently selected from —Cl, —F, —Br, —I, —ON, and —$NO_2$;
$R^3$ is selected from $C_1$-$C_6$ alkyl, —$C_2$-$C_6$ alkenyl, and —$C_2$-$C_6$ alkynyl;
$R^4$ is —H or $C_1$-$C_4$alkyl;
$R^6$ is selected from —H, —$C_1$-$C_{20}$ alkyl, —Cl, —F, —Br, —I, —CN, and —$CF_3$; and
$R^7$ is —($C_{zero}$-$C_4$ alkylene)-(($C_6$-$C_{14}$)aryl) or —($C_{zero}$-$C_4$ alkylene)-((5-15 membered) heteroaryl); wherein each $R^7$ is optionally substituted with from one to three substituents independently selected from —OH, —$C_1$-$C_6$ alkyl, —$C_1$-$C_6$ alkoxy, —Cl, —F, —Br, —I, —CN, and —$NO_2$; or
a pharmaceutically acceptable salt thereof.

11. A compound according to claim 10, wherein:
$R^1$ is —($CH_2$)-(($C_6$-$C_{14}$)aryl) or —CH(OH)—(($C_6$-$C_{14}$)aryl), wherein said aryl is optionally substituted with from one to three substituents $R^{1b}$;
$R^{1b}$ is in each instance independently selected from —F;
$R^3$ is $C_1$-$C_6$ alkyl;
$R^4$ is —H;
$R^6$ is selected from —H, —$C_1$-$C_{20}$ alkyl, —Cl, —F, —Br, —I, —CN, and —$CF_3$; and
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, —F, —Br, —I, —CN, and —$NO_2$; or
a pharmaceutically acceptable salt thereof.

12. A compound according to claim 10, wherein:
$R^1$ is —($CH_2$)-(($C_6$-$C_{14}$)aryl) or —CH(OH)—(($C_6$-$C_{14}$)aryl), wherein said aryl is optionally substituted with from one to three substituents $R^{1b}$;

$R^{1b}$ is in each instance independently selected from —F;
$R^3$ is n-propyl;
$R^4$ is —H;
$R^6$ is —H; and
$R^7$ is ($C_6$-$C_{14}$)aryl or (5-15 membered) heteroaryl; wherein each $R^7$ is optionally substituted with from one to three substituents independently selected from —OH, —$C_1$-$C_6$ alkyl, —$C_1$-$C_6$ alkoxy, —Cl, —F, —Br, —I, —CN, and —$NO_2$; or a pharmaceutically acceptable salt thereof.

13. A compound according to claim 10, wherein:
$R^1$ is —($CH_2$)-(($C_6$-$C_{14}$)aryl) or —CH(OH)—(($C_6$-$C_{14}$)aryl), wherein said aryl is optionally substituted with from one to three substituents $R^{1b}$;
$R^{1b}$ is in each instance independently selected from —F;
$R^3$ is n-propyl;
$R^4$ is —H;
$R^6$ is —H; and
$R^7$ is ($C_6$-$C_{14}$)aryl, wherein said aryl substituted with from one to three substituents independently selected from —OH, —$C_1$-$C_6$ alkyl, —$C_1$-$C_6$ alkoxy, —Cl, —F, —Br, —I, —CN, and —$NO_2$; or a pharmaceutically acceptable salt thereof.

14. A compound according to claim 10, wherein:
$R^1$ is —($CH_2$)-(($C_6$-$C_{14}$)aryl) or —CH(OH)—(($C_6$-$C_{14}$)aryl), wherein said aryl is optionally substituted with from one to three substituents $R^{1b}$;
$R^{1b}$ is in each instance independently selected from —F;
$R^3$ is n-propyl;
$R^4$ is —H;
$R^6$ is —H; and
$R^7$ is (5-15 membered) heteroaryl, wherein said heteroaryl is optionally substituted with from one to three substituents independently selected from —OH, —$C_1$-$C_6$ alkyl, —$C_1$-$C_6$ alkoxy, —Cl, —F, —Br, —I, —CN, and —$NO_2$; or a pharmaceutically acceptable salt thereof.

15. A pharmaceutical composition comprising a compound according to claim 1, or a pharmaceutically acceptable salt thereof, and a pharmaceutically acceptable carrier.

16. A pharmaceutical composition comprising a compound according to claim 10, or a pharmaceutically acceptable salt thereof, and a pharmaceutically acceptable carrier.

* * * * *